(12) United States Patent
Sundstrom

(10) Patent No.: US 6,706,688 B2
(45) Date of Patent: Mar. 16, 2004

(54) METHODS FOR REGULATING BUD-HYPHA TRANSITIONS AND CAMP LEVELS BY THE ADENYLATE CYCLASE-ASSOCIATED PROTEIN GENE, CAP1

(76) Inventor: Paula Sundstrom, 247 E. Beck St., Columbus, OH (US) 43206

( * ) Notice: Subject to any disclaimer, the term of this patent is extended or adjusted under 35 U.S.C. 154(b) by 33 days.

(21) Appl. No.: 09/801,774

(22) Filed: Mar. 9, 2001

(65) Prior Publication Data

US 2003/0104994 A1 Jun. 5, 2003

(51) Int. Cl.$^7$ .................. A61K 38/00; C12P 19/34; C12N 9/00; C12N 1/14; C07H 21/04
(52) U.S. Cl. .................. 514/12; 435/183; 435/91.1; 435/254.22; 536/23.2; 530/333; 424/54
(58) Field of Search .................. 514/12; 435/183, 435/254.22, 91.1; 536/23.2; 530/333; 424/54

(56) References Cited

U.S. PATENT DOCUMENTS

| | | | |
|---|---|---|---|
| 5,627,153 A | 5/1997 | Little, II et al. | |
| 5,652,332 A | 7/1997 | Little, II | |
| 5,733,872 A | 3/1998 | Little | |
| 5,763,567 A | 6/1998 | Little | |
| 5,858,974 A | 1/1999 | Little, II et al. | |
| 5,863,762 A | 1/1999 | Buratowski et al. | |

FOREIGN PATENT DOCUMENTS

| | | |
|---|---|---|
| WO | WO 90/06997 | 6/1990 |
| WO | WO 92/15676 | 9/1992 |
| WO | WO 00/63442 | 10/2000 |

OTHER PUBLICATIONS

Castilla, R. et al. "N– Acetyl–D– Glucosamine Induces Germination in *Candida albicans* through a Mechanism Sensitive to Inhibitors of cAMP–Dependent Proten Kinase" Cell.Signal, vol. 10, No. 10, pp. 713–719, 1998.*
Zhang, X et al. "Analysis of the oxidative stress regulation of the *Candida albicans* transcription factor, Cap1p", Molecular Microbiology, vol. 36, No. 3, pp. 618–629, 2000.*
Alspaugh, A.J. et al. "*Cryptococcus neoformans* mating and virulence are regulated by the G–protein alpha subunit GPA1 and cAMP"., Genes & Development vol. 11, pp. 3206–3217, 1997.*
Kronstad,J. et al. "Control of filamentous growth by mating and cAMP in Ustilago"., Canadian Journal of Botany, vol. 73, Suppl.1,pp. S258–S265, 1995.*
Kronstad, J. et al. "Signaling via cAMP in fungi: interconnections with mitogen–activated protein kinase pathways", Arch Microbiology, vol. 170, pp. 395–404, 1998.*
Bahn et al. sequence alignment report Accession # Q7Y873.*
Castilla et al. ,Cell. Signal. vol. 10, No. 10, pp. 713–719, 1998.*

Csank et al. , Molecular Biology of the Cell, vol. 8, pp. 2539–2551, 1997.*
Bruckmann et al. ,Microbiology vol. 146, pp. 2755–2764, 2000.*
Anderson and Soll, 132 J. Gen. Microbiol. 2035–47 (1986).
Anderson, 2 Hum. Gene Ther. 99–100 (1991).
Anderson, 256 Science 808–13 (1992).
Andreason et al., 6 Biotechniques 650–60 (1988).
Barlow et al., 82 Pt. 2 J. Gen. Microbiol. 261–72 (1974).
Barr et al., 254 Science 1507–9 (1991).
Baum and Perrimon, 10(16) Curr. Biol. 964–73 (2000).
Behr et al., 86 Proc. Natl. Acad. Sci. USA 6982–6 (1989).
Birse et al., 61 Infect. Immun. 3648–55 (1993).
Boeke et al., 197 Mol. Gen. Genet. 345–6 (1984).
Brash et al., 7 Mol. Cell. Biol. 2031–4 (1987).
Caddick, Molecular Biology of Filamentous Fungi 141–52 (1992).
Calera et al., 67 Infect. Immun. 4280–4 (1999).
Calera et al., 68 Infect. Immun. 518–25 (2000).
Cappecchi, 22 Cell 479–88 (1980).
Castilla et al., 10 Cell Signal 713–9 (1998).
Cepko et al., 37 Cell 1053–62 (1984).
Chapman et al., 71 Circ. Res. 27–33 (1992).
Chattaway et al., 123 J. Gen. Microbiol. 233–40 (1981).
Chen et al., 20 Mol. Cell. Biol. 8696–708 (2000).
Cho et al., 30 J. Med. Vet. Mycol. 35–42 (1992).
Clapp et al., 78 Blood 1132–9 (1991).
Cox et al., 15(8) Yeast 703–13 (1999).
Csank et al., 66 Infect. Immun. 2713–21 (1998).
Dabrowa et al., 13 Infect. Immun. 830–5 (1976).
Dai et al., 89 Proc. Natl. Acad. Sci. 10892–5 (1992).
DeRisi et al., 11(1) Curr. Opin. Oncol. 76–9 (1999).
Egidy et al., 13 Exp. Mycol. 428–32 (1989).
Fedor–Chaiken 61 Cell 329–40 (1990).
Felgner et al. 349 Nature 351–2 (1991).
Felgner et al., 84 Proc. Natl. Acad. Sci. USA 7413–7 (1987).
Feng et al., 181 J. Bacteriol. 6339–46 (1999).
Field et al., 61 Cell 319–27 (1990).
Fonzi et al., 134 Genetics 717–28 (1993).
Freeman et al., 16(2) Mol. Cell. Biol. 548–56 (1996).
Freeman et al., 270 J. Biol. Chem. 5680–5 (1995).
Fu et al., 4(11) Mol. Microbiol. 1847–52 (1990).
Fu et al., 7(5) Mol. Cell. Biol. 1691–6 (1987).
Gancedo, 25 Fems Microbiol. Rev. 107–23 (2001).

(List continued on next page.)

*Primary Examiner*—Rodney P Swartz
*Assistant Examiner*—Khatol S Shahnan-Shah
(74) *Attorney, Agent, or Firm*—Preston Gates Ellis & Rouvelas Meeds LLP

(57) ABSTRACT

The infection of a mammalian host by a microorganism can be prevented or treated through the disruption of the *C. albicans* homologue of adenylate cyclase-associated protein gene. These methods may be used in the identification, prevention or treatment of microbial infection of mammalian hosts such as immunocompromised or immunosuppressed humans, for example, those having AIDS or undergoing transplantation or anti-cancer therapy.

34 Claims, 11 Drawing Sheets

OTHER PUBLICATIONS

Ghannoum et al., 63 Infect. Immun. 4528–30 (1995).
Gimeno et al., 68(6) Cell 1077–90 (1992).
Griffioen, et al., 275 J. Biol. Chem. 1449–56 (2000).
Haas et al., 27(2) Curr. Genet. 150–8 (1995).
Hall et al., 17 EMBO J. 4370–8 (1998).
Hazen et al., 24 Infect. Immun. 661–6 (1979).
Higgins & Sharp, 73 Gene 237–44 (1988).
Hilberg et al., 84 Proc. Natl. Acad. Sci. USA 5232–6 (1987).
Holland et al., 84 Proc. Natl. Acad. Sci. USA 8662–6 (1987).
Holmes et al., 133 J. Gen. Microbiol. 3219–28 (1987).
Houghten et al., 354 Nature 84–6 (1991).
Huang et al., 27(2 Pt. 1) Cell 245–55 (1981).
Iyer et al., 283(5398) Science 83–7 (1999).
Jerne et al., 1 EMBO 234 (1982).
Jerne, 125 Ann. Immunol. 373 (1974).
Johnston, 346 Nature 776–7 (1990).
Kawamukai et al., 3 Mol. Biol. Cell. 167–80 (1992).
Kimura and Pearsall, 21 Infect. Immun. 64–8 (1978).
Kinsman et al., 31 Mycoses 617–26 (1988).
Kohler and Fink, 93 Proc. Natl. Acad. Sci. USA 13223–8 (1996).
Kohler et al. 6 Eur. J. Immunol. 511–19 (1976).
Kohler et al., 256 Nature 495–97 (1975).
Kronstad et al., 170 Arch. Microbiol. 395–404 (1998).
Kübler et al., 272 J. Biol. Chem. 20321–3 (1997).
Kudla et al., 9(5) EMBO J. 1355–64 (1990).
Kulkarni et al., 5 Exp. Mycol. 148–54 (1981).
Kurtz et al., 6 Mol. Cell. Biol. 142–9 (1986).
Lam et al., 354 Nature 82–4 (1991).
Lambrechts et al., 93 Proc. Natl. Acad. Sci. USA 8419–24 (1996).
Land et al., 11(5) Infect. Immun. 1014–23 (1975).
Larrick et al., Gene Therapy. Application of Molecular Biology 71–104 (Elsevier Science Publishing Co., Inc.) (1991).
Leberer et al., 7 Curr. Biol. 539–46 (1997).
Leclerc et al., 90 J. Clin. Invest. 936–44 (1992).
Lengeler et al., 64 Microbiol. Mol. Biol. Rev. 746–85 (2000).
Lila and Drubin, 8 Mol. Biol. Cell. 367–85 (1997).
Lim et al., 83 Circulation 2007–11 (1991).
Lo and Dranginis, 9 Mol. Biol. Cell. 161–71 (1998).
Lo et al., 90 Cell 939–49 (1997).
Loeb et al., 19 Mol. Cell. Biol. 4019–27 (1999).
Loeffler et al., 54 J. Neurochem. 1812–5 (1990).
Lorenz and Heitman 16 EMBO J. 7008–18 (1997).
Lorenz et al., 154 Genetics 609–22 (2000).
Lynch et al., 89 Proc. Natl. Acad. Sci. USA 1138–42 (1992).
Marzluf, 61(1) Microbiol. Mol. Biol. Rev. 17–21 (1997).
Matviw et al., 12 Mol. Cell. Biol. 5033–40 (1992).
Miller et al. in Hybridomas in Cancer Diagnosis and Therapy 134 (1982).
Miller, 357 Nature 455–60 (1992).
Miller, 76 Blood 271–8 (1990).
Minehart et al., 11(12) Mol. Cell. Biol. 6216–28 (1991).
Mösch and Fink, 145 Genetics 671–84 (1997).
Mösch et al., 10 Mol. Biol. Cell. 1325–35 (1999).
Nabel et al., 244 Science 1342–4 (1989).
Niimi et al., 142 J. Bacteriol. 1014–4 (1980).
Niimi, 20 Fungal Genet. Biol. 79–83 (1996).
Palmer et al., 88 Proc. Natl. Acad. Sci. USA 1330–34 (1991).
Quantin et al., 89 Proc. Natl. Acad. Sci. USA 2581–4 (1992).
Reimann et al., 89 J. Immunol. Meth. 93–101 (1986).
Roemer et al., 208 Eur. J. Biochem. 211–25 (1992).
Roman et al., 18 Som. Cell. Mol. Gen. 247–58 (1992).
Rupp et al., 18 EMBO J. 1257–69 (1999).
Schaller et al., 34 Mol. Microbiol. 169–80 (1999).
Scharfmann et al., 88 Proc. Natl. Acad. Sci. USA 4626–30 (1991).
Schweizer et al., 38 Mol. Microbiol. 435–45 (2000).
Selden et al., 317 New Eng. J. Med. 1067–76 (1987).
Sobel et al., 44 Infect. Immun. 576–80 (1984).
Songyang et al., 72 Cell 767–78(1993).
Staab et al., 271 J. Biol. Chem. 6298–305 (1996).
Staab et al., 283 Science 1535–38 (1999).
Staib et al., 97 Proc. Natl. Acad. Sci. USA 6102–7 (2000).
Stewart et al., 46(2–3) Gene 291–5 (1986).
Straus, The Adenovirus 451–96 (H.S. Ginsberg, ed., Plenum Press) (1984).
Sundstrom et al., 174 J. Bacteriol. 6789–99 (1992).
Temin, Retrovirus vectors for gene transfer, in Gene Transfer 149–87 (Kucherlapati, ed., Plenum) (1986).
Terrell, 74 Mayo Clin. Proc. 78–100 (1999).
Toda et al., 40 Cell 27–36 (1985).
Valerio et al., 84 Gene 419–27 (1989).
Vojtek and Cooper, 105 J. Cell. Sci. 777–85 (1993).
Wolff et al., 247 Science 1465–8 (1990).
Yamada–Okabe et al., 181 J. Bacteriol. 7243–7 (1999).
Yanagita, 26 Arch. Microbiol. 329–44 (1957).
Yu et al., 274 J. Biol. Chem. 19985–91 (1999).
Zelada et al., 42 Cell. Mol. Biol. (Noisy–le–grand) 567–76 (1996).
Zelicof et al., 271 J. Biol. Chem. 18243–52 (1996).

* cited by examiner

| Strain | Genotype | Parent Strain | References |
|---|---|---|---|
| SC5314 | Wild type | | Gillum et al., 198 MOL. GEN. GENET. 179-82 (1984) |
| CAI4 | Δura3::imm434/Δura3::imm434 | SC5314 | Fonzi et al., 134 GENETICS 717-28 (1993) |
| *UnoPP-1 | Δura3::imm434/Δura3::imm434 Δeno1::URA3/ENO1 | CAI4 | Postlethwait et al., 177 J. BACTERIOL. 1772-9 (1995) |
| CAC1 | Δura3::imm434/Δura3::imm434 CAP1/cap1::hisG-URA3-hisG | CAI4 | This study |
| CAC1-1 | Δura3::imm434/Δura3::imm434 CAP1/cap1::hisG | CAC1 | This study |
| CAC1-1A | Δura3::imm434/Δura3::imm434 cap1::hisG-URA3-hisG | CAC1-1 | This study |
| CAC1-1A1 | Δura3::imm434/Δura3::imm434 cap1::hisG/cap1::hisG | CAC1-1A | This study |
| CACRE1 | Δura3::imm434/Δura3::imm434 CAP1/cap1::hisG ENO1/eno13 | CAC1-1A1 | This study |

*a CAI4 derivative made Ura+ by disruption of an enolase gene with URA3

Figure 1

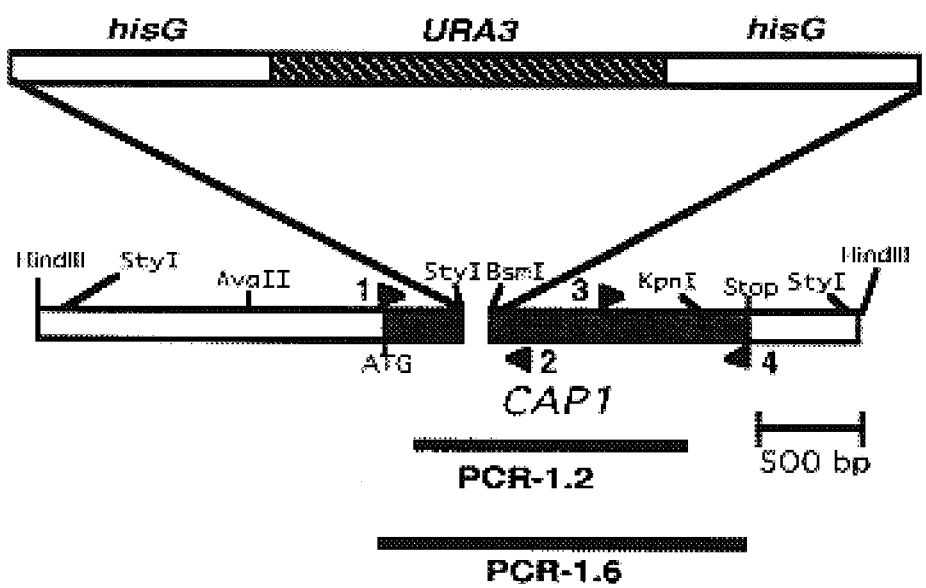
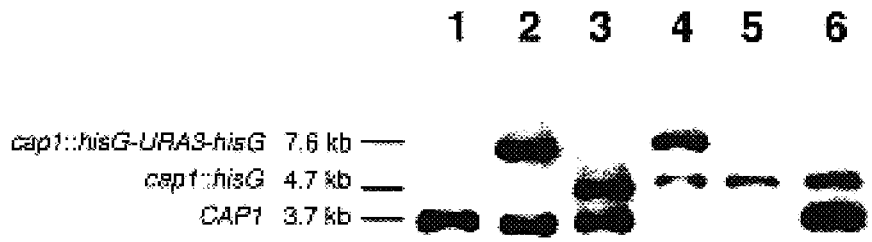
Figure 2

FIG. 3

| Strains | Doubling Time (hour)* | | | | | |
|---|---|---|---|---|---|---|
| | Rich media (YPD) | | | Minimal media (YNB) | | |
| | 27°C | 30°C | 37°C | 27°C | 30°C | 37°C |
| UnoPP-1 | 2.2 | 1.6 | 2.0 | 2.9 | 2.9 | 3.0 |
| CAC1 | 2.2 | 1.7 | 2.0 | 2.9 | 2.9 | 3.0 |
| CAC1-1A | 2.3 | 1.7 | 2.2 | 3.9 | 3.7 | 3.8 |
| CACRE1 | 2.2 | 1.7 | 2.1 | 2.8 | 2.9 | 2.9 |

*Mean value from two independent experiments that differed by less than 20%

Figure 5

A
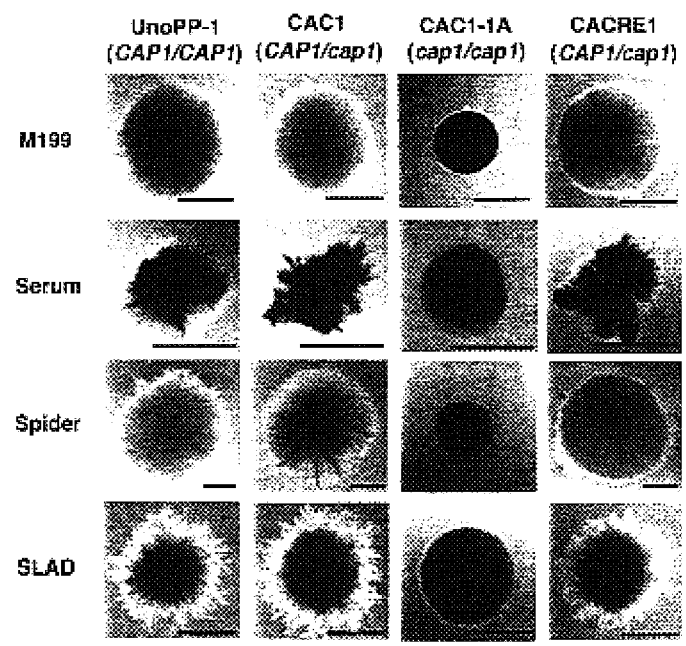
B
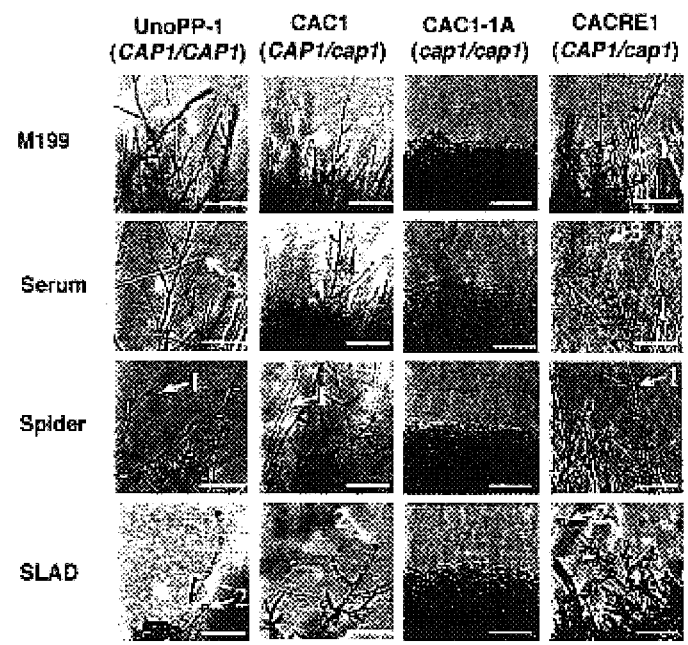
Figure 7

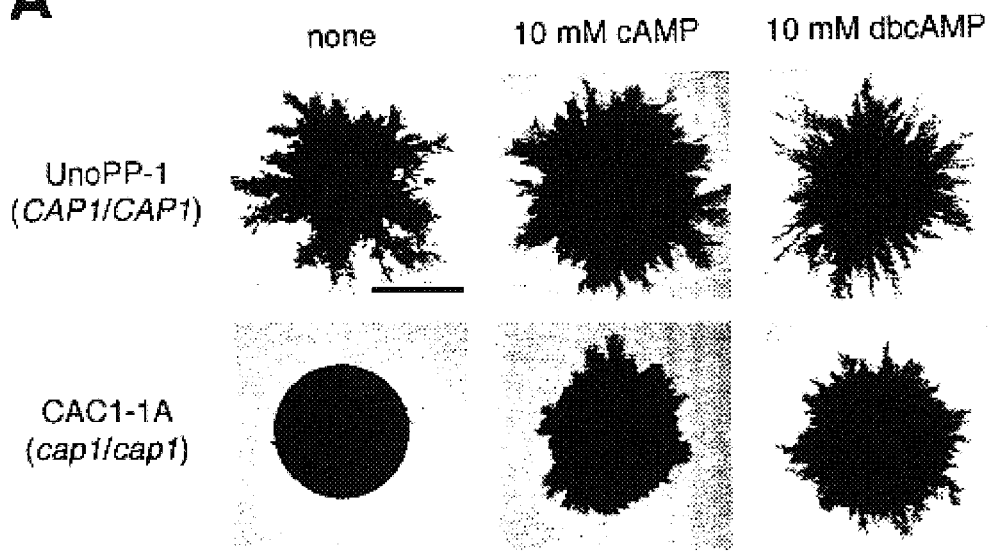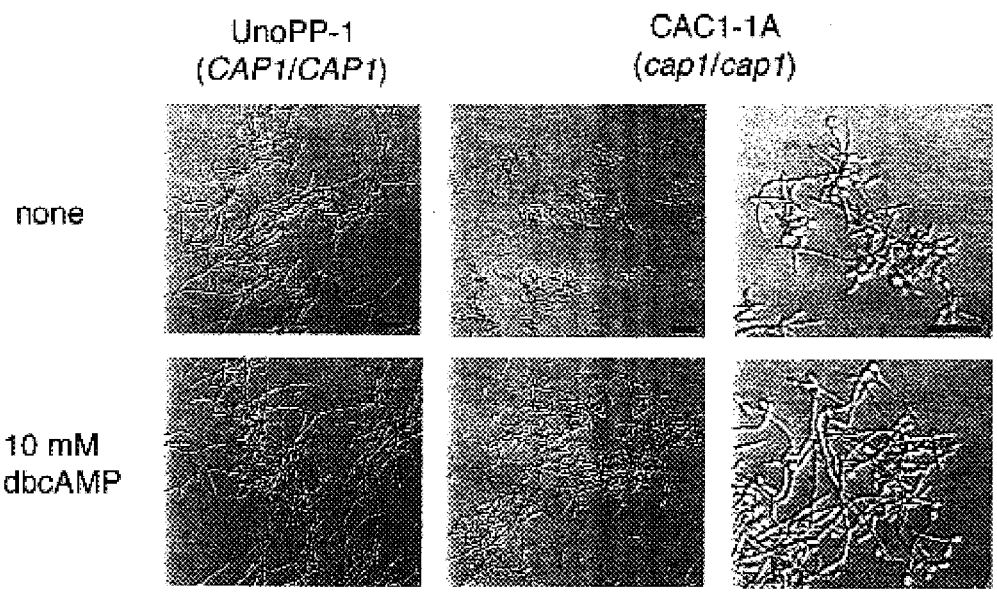
Figure 9

METHODS FOR REGULATING BUD-HYPHA TRANSITIONS AND CAMP LEVELS BY THE ADENYLATE CYCLASE-ASSOCIATED PROTEIN GENE, CAP1

STATEMENT REGARDING FEDERALLY SPONSORED RESEARCH

This invention was made, at least in part, with U.S. government support under grant No. 2R01DE011375, awarded by NIH. The U.S. government may have certain rights in the invention.

FIELD OF THE INVENTION

The present invention relates to methodologies and molecular targets for the prevention and treatment of microbial infection of a mammalian host through the disruption of the *Candida albicans* homologue of adenylate cyclase-associated protein (CAP1) gene. Preferably, these methods and molecular targets may be used in the prevention and treatment of microbial infection of mammalian hosts such as immunocompromised patients at risk for opportunistic fungal infections, organ transplant patients, cancer patients undergoing chemotherapy, burn patients, AIDS patients, or patients with diabetic ketoacidosis.

BACKGROUND OF THE INVENTION

Whether pathogenic or opportunistic, microorganisms have evolved numerous mechanisms to facilitate their establishment and proliferation in mammalian hosts. During initial infection, the interaction of a microorganism with its mammalian host can include attachment or adhesion to the host cell surface, and invasion of host cells, for example. In certain instances, this interaction can be nonspecific. In others, such microbial interaction involves the specific binding of the microorganism to a particular receptor or receptor complex expressed on the host cell surface. In turn, the binding event can trigger changes in the microorganism and/or the mammalian host cell, leading to the progression of infection.

Candida is an ubiquitous yeast recognized as the causative agent of candidiasis (*Candida mycosis*). At least 90% of the disorders are caused by the species *Candida albicans*, which is an opportunistic yeast that elicits only mild superficial infections in normal individuals. However, destabilization of the host-parasite equilibrium upon inopportune loss or deficiencies in protective innate and immune deterrents favors overgrowth of the common gastrointestinal tract denizen and opportunistic pathogen, *C. albicans*. Acquired immunodeficiency syndrome (AIDS) or iatragenic immunosuppression are risk factors for oropharyngeal and esophageal candidiasis (Hood et al., 28 Clin. Infect. Dis. 587–96 (1999)). Thus, oropharyngeal and esophageal candidiasis are among the most frequent opportunistic fungal infections observed in human immunodeficiency virus positive (HIV+) and AIDS patients, occurring in the majority of patients. Candidal infections increase in severity and recur more frequently as the immunodeficiency progresses. The current status of the AIDS epidemic is one of increasing numbers of individuals infected and no cure. Many infected individuals may live for a long time with HIV in an essentially permanent immunocompromised state. Because of the loss of the cellular component of the immune system, AIDS patients are susceptible to invasion of submucosal tissue by *C. albicans*. In addition to HIV infected patients, oral candidiasis occurs in patients with leukemia or other cancers, as well as in patients with other underlying diseases. Prematurely-born infants are also at risk and may acquire mucosal infections causing permanent sequelae (Huang et al., 30 Scand. J. Infect. Dis. 137–42 (1998); Sood et al., 41 MYCOSES 417–9 (1998)). Candidiasis in denture wearers, or denture stomatitis, is the most common of all *C. albicans* associated diseases.

Although *C. albicans* is sensitive to antifungal drugs, treatment over long periods of time are required. At present, the treatment for invasive infections is based on relatively few antimycotics. Nystatin, ketoconazole, and amphotericin B are drugs which are used to treat oral and systemic Candida infections. However, orally administered nystatin is limited to treatment within the gut and is not applicable to systemic treatment. Some systemic infections are susceptible to treatment with ketoconazole or amphotericin B, but these drugs may not be effective in such treatment unless combined with additional drugs. Amphotericin B has a relatively narrow therapeutic index and numerous undesirable side effects and toxicities occur even at therapeutic concentrations. While ketoconazole and other azole anti fungals exhibit significantly lower toxicity, their mechanism of action, inactivation of cytochrome $P_{450}$ prosthetic group in certain enzymes (some of which are found in humans), precludes use in patients that are simultaneously receiving other drugs that are metabolized by the body's cytochrome $P_{450}$ enzymes. See, e.g., U.S. Pat. No. 5,863,762.

Other known antifungal agents include: polyene derivatives, such as amphotericin B (including lipid or liposomal formulations thereof) and the structurally related compounds nystatin and pimaricin; flucytosine (5-fluorocytosine); azole derivatives (including ketoconazole, clotrimazole, miconazole, econazole, butoconazole, oxiconazole, sulconazole, tioconazole, terconazole, fluconazole, itraconazole, voriconazole [Pfizer] and SCH56592 [Schering-Plough]); allylamines-thiocarbamates (including tolnaftate, naftifine and terbinafine); griseofulvin; ciclopirox; haloprogin; echinocandins (including MK-0991 [Merck]); nikkomycins; and bactericidal/permeability-increasing protein (BPI), described in U.S. Pat. Nos. 5,627,153; 5,858,974; 5,652, 332; 5,763,567; and 5,733,872. Unfortunately, antimycotics cause serious, sometimes different, side effects, such as renal insufficiency, hypocalcemia and anemia, as well as unpleasant constitutional symptoms such as fever, shivering and low blood pressure.

The frequency of candidal infections may be a result of the prophylactic use of antibacterial drugs used in AIDS patients to minimize other opportunistic infections. Emergence of drug-resistant isolates and the limited selection of antifungal drugs point to the need for research aimed at identifying new anti-fungal targets (Terrell, 74 Mayo Clin. Proc. 78–100 (1999)). However, the pathogenesis is complex and is thought to involve multiple host factors that include loss of cell mediated immunity and altered phagocytic cell activity. High frequencies of nosocomial candidemia reflect the ability of *C. albicans* to translocate across the gastrointestinal tract, disrupting internal tissues in debilitated patients (Viscoli et al., 28 Clin. Infect. Dis. 1071–9 (1999)).

Thus far, studies have shown that development of candidiasis is a multi-stage process requiring sensing environmental conditions and transducing signals to regulate expression of appropriate genes at balanced levels in *C. albicans*. Filamentous growth of *C. albicans* includes not only pseudohyphal, elongated yeast-like forms described for *Saccharomyces cerevisiae*, but true hyphae as well. Compared to most pathogenic fungi, the morphological response of *C. albicans* to environmental conditions is rapid. Germ tubes are produced within one hour of placing cells in appropriate conditions. The mechanisms employed by *C. albicans* to achieve this apparently advantageous spectrum of growth morphologies and optimized metabolic activities are poorly understood.

A feature of *C. albicans* growth that is correlated with pathogenicity in the oral cavity is the ability to transform from budding to filament-extending growth. Filamentous forms adhere more readily to buccal epithelial cells than budding yeasts, and histologically are a prominent feature of invasion of the mucosa. In mucosal disease, filamentous forms, particularly true hyphae, invade the keratinized layer of differentiated, stratified squamous epithelium. True hyphae are septate, cylindrical structures with parallel sides that are formed by extension of germ tubes that emerge from yeasts in appropriate environmental conditions.

The relative contribution of yeast and filamentous forms to the pathogenesis of candidiasis is an unresolved issue. However, mutants that do not produce hyphae in vitro have reduced virulence in animal models (Ghannoum et al., 63 Infect. Immun. 4528–30 (1995); Lo et al., 90 CELL 939–49 (1997); Sobel et al., 44 Infect. Immun. 576–80 (1984)). Expression of hypha-specific virulence factors such as the hyphal wall protein (HWP1) adhesin gene (Staab et al., 283 Science 1535–38 (1999); Staab et al., 271 J. Biol. Chem. 6298–305 (1996)) and secreted aspartyl proteinase (SAP) genes (Schaller et al., 34 Mol. Microbiol. 169–80 (1999); Staib et al., 97 Proc . Natl. Acad. Sci. USA 6102–7 (2000)) are correlated with the virulence of hyphal forms. Research into the mechanisms that lead to the production of these virulence factors is important for developing strategies to interfere with candidiasis.

Thus, an alternative method to the prevention and treatment of candidiasis may be approached via disruption of molecular events that transform *C. albicans* to the pathogenic filamentous form. In many pathogenic fungi, interconversions between morphological growth forms, particularly between yeast growth and filamentous growth coincide with adaptation to a host environment followed by tissue destruction. Morphological interconversions in fungi are dependent upon signal transduction pathways including the cyclic AMP (cAMP)-dependent protein kinase A (PKA) pathway (Bruno et al., 15 EMBO J. 5772–82 (1996); Gancedo, 25 FEMS Microbiol. Rev. 107–23 (2001); Kronstad et al., 170 Arch. Microbiol. 395–404 (1998); Lengeler et al., 64 Microbiol. Mol. Biol. Rev. 746–85 (2000)). For the plant pathogens *Ustilago maydis* and *Magnaporthe grisea*, cAMP signaling is important for the establishment of filamentous growth in the former and for formation of the infecting appressorium structure of the later (Kronstad et al., supra; Lengeler et al., supra).

Knowledge about how cAMP signaling mediates morphological interconversion is best understood for *S. cerevisiae*, a budding yeast that produces elongated pseudohyphal cells and forms filamentous colonies in the presence of limiting nitrogen (Gancedo, supra; Lengeler et al., supra). Pseudohyphal cells exhibit unipolar budding, do not separate and invade agar (Gimeno et al., 68 Cell 1077–90 (1992)). Recent experiments involving gene disruption and epistasis analyses have elucidated both upstream and downstream elements of the cAMP dependent pseudohyphal growth pathway in *S. cerevisiae* (Gancedo, supra; Kronstad et al., supra; Lengeler et al., supra). Adenylate cyclase is activated either through a receptor (Gpr1) that is coupled to a G protein (Gpa2) or by Ras2 (Gimeno et al., supra; Kübler et al., 272 J. Biol. Chem. 20321–3 (1997); Lorenz and Heitman 16 EMBO J. 7008–18 (1997); Lorenz et al., 154 Genetics 609–22 (2000); Mösch et al., 10 Mol. Biol. Cell. 1325–35 (1999); Toda et al., 40 Cell 27–36 (1985)). The subsequent activation of PKA then results in activation of the Flo8 transcription factor to produce a mucin-like protein, Flo11, that is localized to the cell surface and is required for pseudohyphal growth (Lambrechts et al., 93 Proc. Natl. Acad. Sci. USA 8419–24 (1996); Lo and Dranginis, 9 Mol. Biol. Cell. 161–71 (1998); Pan and Heitman, 19 Mol. Cell. Biol. 4874–87 (1999); Rupp et al., 18 EMBO J. 1257–69 (1999)). Although cross-talk between mitogen-activated protein kinase (MAPK) and cAMP signaling pathways is evident (Mösch et al., supra), transcription factor targets important for filamentous growth appear not to be shared by the two pathways (Gancedo, supra; Lengeler et al., supra). Pseudohyphal defects caused by mutations in STE12 of the MAPK pathway and PHD1 are suppressed by constitutive activation of PKA through deletion of the regulatory subunit gene (BCY1) (Lo and Dranginis, supra).

Biochemical studies implicate cAMP increases in promoting bud-hypha transitions. Intracellular levels of cAMP increase and, under nutrient limitation, exogenous cAMP or dibutyryl cAMP (dbcAMP) increases the frequency of bud-hypha transitions (Chattaway et al., 123 J. Gen. Microbiol. 233–40 (1981); Niimi, 20 Fungal Genet. Biol. 79–83 (1996); Niimi et al., 142 J. Bacteriol. 1010–4 (1980); Zelada et al., 42 Cell. Mol. Biol. (Noisy-le-grand) 567–76 (1996)). Inhibitors of cAMP phosphodiesterase or cAMP-dependent protein kinase induce or block germ tube formation, respectively (Castilla et al., 10 Cell. Signal. 713–9 (1998), Chattaway et al., supra). However, genetic studies involving mutational analysis of genes that control cAMP levels and assessment of their roles in regulating bud-hypha transitions and filamentous growth have not been reported. Studies of the role of cAMP dependent signaling in morphogenesis will also bring to light common virulence pathways for distantly related fungal pathogens.

In *S. cerevisiae*, Ras activation of adenylate cyclase involves the adenylate cyclase protein (CAP, also known as Srv2p) (Fedor-Chaiken 61 Cell 329–40 (1990); Field et al., 61 Cell 319–27 (1990); Shima et al., 20 Mol. Cell. Biol. 26–33 (2000)). The CAP gene was identified in a genetic screen for mutants that suppressed defective growth of a strain carrying an inducible hyperactive RAS2$^{val119}$ gene (Fedor-Chaiken, supra). The CAP gene was also isolated by screening a yeast cDNA expression library with antisera to a 70-KDa protein that co-purified with adenylate cyclase (Field et al., supra). CAP is required for normal budding morphology and growth rates in nutrient-rich media (Fedor-Chaiken, supra; Field et al., supra). Interestingly, the *S. cerevisiae* CAP gene has been shown to be involved in pseudohyphal differentiation using transposon mutagenesis to screen for mutant strains defective for filamentous growth (Mösch et al., supra). CAPs of mice (Vojtek and Cooper, 105 J. Cell. Sci. 777–85 (1993)) and humans (Matviw et al., 12 Mol. Cell. Biol. 5033–40 (1992)) are 34% identical and 35% similar, respectively, to *S. cerevisiae* CAP showing that CAP genes are conserved throughout evolution. Although CAPs from different organisms have similar primary and secondary structures, the function of CAPs in developmental programs has diverged among fungi. CAP mutants of *Schizosaccharomyces pombe* but not *S. cerevisiae* conjugate and sporulate in inappropriate conditions (Kawamukai et al., 3 Mol. Biol. Cell. 167–80 (1992)).

Modulation of adenylate cyclase activity by CAP in *S. cerevisiae* (Field et al., supra; Yu et al., 274 J. Biol. Chem. 19985–91 (1999)) suggests that the CAP gene of *C. albicans* might affect intracellular cAMP levels, allowing assessment of the role of cAMP in the filamentous growth and virulence of *C. albicans*. In the present invention, the *C. albicans* CAP1 gene was cloned and its identity was established by sequence similarities to CAP gene products of other organisms, by the reduction in cAMP levels in cap1/cap1 mutants and by the ability of exogenous cAMP or dbcAMP to promote bud-hypha transitions and filamentous growth in cap1/cap1 mutants. cap1/cap1 mutants were unconditionally deficient in forming bud-hypha transitions and filamentous growth in rich and minimal, liquid and agar-based culture media, as well as in serum and saliva. cap1/cap1 mutants also showed reduced virulence in a systemic model of candidiasis. The present invention is the first to describe genetic evidence showing that cAMP promotes true hyphae formation in *C. albicans*. The present invention also describes interference with CAP1 function, which has potential for providing novel strategies for interfering with candidiasis.

By defining the molecular events leading to the expression of a morphogenically important gene, and through the identification of new genes that are co-regulated with CAP1, the present invention has strong potential for identifying new and novel ways to interfere with candidiasis. The long term medical benefits of the present invention may be the development of alternative or adjunctive therapies based on new knowledge about expression of CAP1 genes in *C. albicans*. Accordingly, an objective of the present invention includes identifying and characterizing the 5' and 3' sequences flanking the CAP1 gene.

Other objects, features and advantages of the present invention will become apparent from the following detailed description. The detailed description and the specific examples, however, indicate only preferred embodiments of the invention. Various changes and modifications within the spirit and scope of the invention will become apparent to those skilled in the art from this detailed description.

SUMMARY OF THE INVENTION

The present invention relates to a method for disrupting the *C. albicans* homologue of adenylate cyclase-associated protein (CAP1) gene, which results in the interference of morphogenic transitions of the fungus. In a specific embodiment, disruption of the *C. albicans* CAP1 gene prevents the expression of the polypeptide capable of increasing cAMP levels which in turn stimulates bud/hypha transition. This particular embodiment of the present invention is accomplished through the construction of a cap1/cap1 mutant.

Another aspect of the invention is a purified polypeptide comprising the amino acid sequence of SEQ. ID. NO. 1, wherein said polypeptide *C. albicans* Cap1 is the gene product of the CAP1 gene (SEQ. ID. NO. 2). Another aspect is an isolated DNA molecule encoding the polypeptide having the amino acid sequence of SEQ. ID. NO. 1, and an isolated DNA molecule comprising the nucleotide sequence SEQ. ID. NO. 2 encoding the polypeptide of SEQ. ID. NO. 1. A further aspect is a nucleic acid capable of hybridizing under high stringency conditions to the DNA molecule of an isolated DNA molecule comprising the nucleotide sequence SEQ. ID. NO. 2 encoding the polypeptide of SEQ. ID. NO. 1.

An additional aspect of the invention is a microarray comprising at least one nucleotide sequence or fragment thereof, of the CAP1 gene (SEQ. ID. NO. 2). A further aspect is a method for detecting the expression of a protein capable of stimulating increases in cAMP levels in a microorganism, using microarrays and genome-wide expression. In a preferred embodiment, the microorganism is a bacteria or yeast, and more preferably *C. albicans*.

In yet a further embodiment of the present invention, the patients may be immunocompromised and at risk for opportunistic fungal infections. In particular the patient may be, but is not limited to, an organ transplant recipient, a cancer patient undergoing chemotherapy, a burn patient, an AIDS patients, or a patient with diabetic ketoacidosis.

In a final embodiment, the present invention provides a methodology for characterizing genes under the control of Cap1 in a fungus. This embodiment is accomplished by creating a genomic library isolated from a fungus, specifically *C. albicans*, screening the genomic library with probes for genes identified by genome-wide expression profiling, and isolating and sequencing the resultant clones.

BRIEF DESCRIPTION OF THE DRAWINGS

FIG. 1 shows a table of the *Candida albicans* strains used in the present invention.

FIGS. 2A–2B represent the disruption of *C. albicans* CAP1. FIG. 2A is the genetic organization of the CAP1 locus. The CAP1 open reading frame (shaded bar) and PCR products (solid line) (PCR-1.2 and PCR-1.6) are indicated. Each arrow head indicates primers used for RT-PCR to confirm the disruption of CAP1 (arrow 1: CAP-NRT 1, arrow 2: CAP-F1, arrow 3: CAP-R3, arrow 4: CAP-3F1). FIG. 2B depicts a Southern blot analysis of HindIII-digested *C. albicans* genomic DNA probed with PCR-1.2. Lanes 1–6 show parental strain CAI4 (lane 1); CAP1/CAP1 strains CAC1 and CAC1-1, Ura$^+$ and Ura$^-$ respectively (lanes 2 and 3); homozygous cap1/cap1 strains CAC1-1A and CAC1-1A1 Ura$^+$ and Ura$^-$ respectively (lanes 4 and 5); and CAP1 complemented strain CACRE1 (lane 6).

FIG. 3 depicts the primary structure alignment of *C. albicans* Cap1 with CAPs of other organisms. Multiple sequence alignments of CAPs from *C. albicans* (CaCAP1), *S. cerevisiae* (ScCAP), *S. pombe* (SpCAP), Mouse (MouseCAP1), and Human (HumanCAP1) were performed with ClustalW (Thompson et al., 22 Nucl. Acids Res. 4673–80 (1994)) and illustrated with MacVector 6.5.3 (Oxford Molecular Company). Solid lines indicate residues for the conserved RLE/RLE motif (Hazen et al., 24 Infect. Immun. 661–6 (1979); Hood et al., 28 Clin. Infect. Dis. 587–96 (1999); Huang et al., 30 Scand. J. Infect. Dis. 137–42 (1998); Kawamukai et al., supra; Kawarabayashi et al., 28 Gynecoyal. Obstet. Invest. 132–7 (1989); Kimura and Pearsall, 21 Infect. Immun. 64–8 (1978); Kohler and Fink, 93 Proc. Natl. Acad. Sci. USA 13223–8 (1996); Kurtz et al., 6 Mol. Cell. Biol. 142–9 (1986); Kyte and Doolittle, 157 J. Mol. Biol. 105–32 (1982); Lebrerer et al., 7 Curr. Biol. 539–46 (1997)), the polyproline region (289–297) and two consensus SH3-binding motifs (358–361 and 364–367) *C. albicans*.

FIG. 5 shows a table of the time required for *C. albicans* strains to double in numbers.

FIGS. 7A–7B depict the phenotypic analyses of cap1/cap1 mutants in agar media. cap1/cap1 strains were defective in filamentous growth. Colonial appearances (FIG. 7A) and cellular morphologies at colony rims (FIG. 7B), respectively, in each agar media condition are shown. FIG. 7A depicts colonies of the cap1/cap1 mutant. The colonies consisted of budding yeasts (third columns in FIGS. 7A and 7B), whereas strains with CAP1 (UnoPP-1, CAC1, and CACRE1) produced filamentous growths of differing characteristics depending on the media. The asymmetric colonies formed by strains with CAP1 in serum contained infrequent thick plumes composed of filaments covered with buds radiating from the colony center (arrow). FIG. 7B depicts strains with CAP1. These strains produced uniform hyphae with short branches in M199 and Spider plates (arrows "1") or hyphae with thick-walled terminal buds in SLAD media (arrows "2"). In media with serum, colonies of strains with CAP1 were composed primarily of hyphae bereft of buds (arrows "3"). M199 plates were incubated first at 30° C. for 48 h and transferred to 37° C. for another 48 h, whereas the other plates were incubated for 6 days at 37° C. Black and white bars indicate lengths of 1 mm and 50 $\mu$m, respectively.

FIG. 8A displays germ tube inducing conditions (M199 at 37° C.). cAMP levels (pmol per mg protein) at time zero for UnoPP-1, CAC1, CAC1-1A, and CACRE were 45.3±4.6, 55.1±6.9, 61.8±6.5, and 51.4±6.7 (mean value±standard deviation), respectively. The decreased cAMP level in the cap1/cap1 mutant compared to strains with CAP1 at 1 h was statistically significant (*, p<0.01 (UnoPP-1 or CAC1 vs. CAC1-1A) and p<0.05 (CACRE1 vs. CAC1-1A) using Bonferroni's multiple comparison test performed with Prism 2.0b (GraphPad Software)). FIG. 8B shows budding growth in M199 at 27° C. cAMP levels (pmol per mg protein) at time zero for UnoPP-1, CAC1, CAC1-1A, and CACRE were 50.9±22.4, 58.1±8.4, 37.4±2.9, and 52.6±6.6, respectively. FIG. 8C depicts the morphological changes of UnoPP-1 (CAP1/CAP1), cap1/cap1 strain (CAC1 and CACRE1) and cap1/cap1 strain (CAC1-1A) were monitored during germ tube induction. Bars indicate a length of 5 $\mu$m.

FIGS. 9A–9B depict the suppression of defective bud-hypha transitions and filamentous growth in the cap1/CAP1 mutant by exogenous cAMP or its derivative, dbcAMP. The wild type CAP1/CAP1 strain, UnoPP-1, and the cap1/cap1 mutant strain, CAC1-1A, were grown in (FIG. 9A) SLAD media with or without 10 mM cAMP or dbcAMP for 5 days at 37° C. Bars indicate a length of 1 mm. FIG. 9B depicts bud-hypha transitions induced at cell concentrations of $1 \times 10^6$ cells/ml in pre-warmed M199+serum with or without 10 mM dbcAMP for 13 hours (first (UnoPP-1) and second (CAC1-1A) columns, 20×objective; third (CAC1-1A) column, 40×objective). Bars indicate a length of 30 $\mu$m.

DETAILED DESCRIPTION OF THE INVENTION

Figure 4:
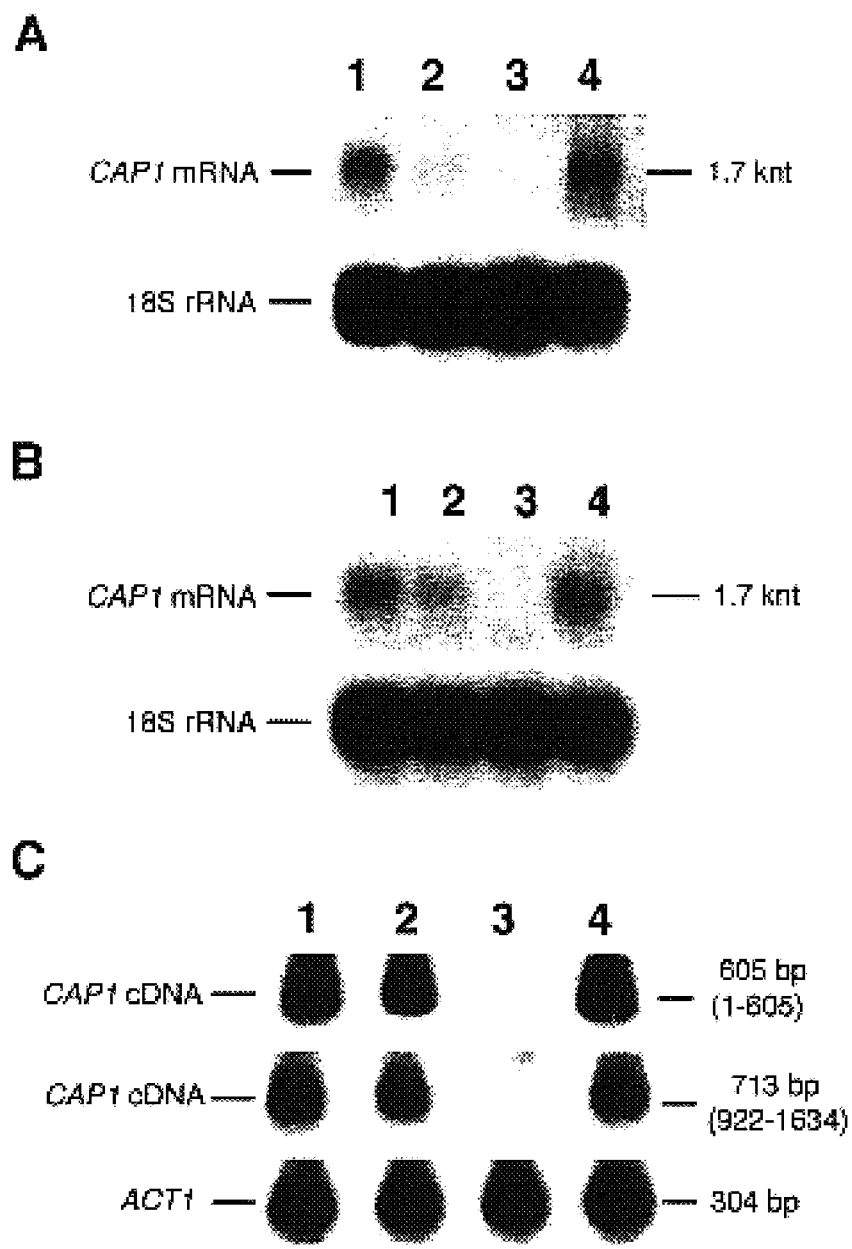
FIGS. 4A–4B depict Northern blot and RT-PCR analysis of cap1/cap1 mutants. CAP1 mRNA is absent in the cap1/cap1 strain and present at equivalent low levels in other strains during yeast growth (FIG. 4A) or germ tube induction (FIG. 4B). Total RNA (7 μg/lane) isolated was separated in a formaldehyde agarose gel transferred to a nitrocellulose membrane, and probed with radiolabeled PCR-1.2 to detect CAP1 mRNA and 18S rRNA as a control. The membrane was exposed to X-ray film for seven days for detection of CAP1 mRNA and for four hours for detection of 18S rRNA.
FIG. 4C depicts amplification of 5'-(605 bp, 1 to 605) and 3'-portions (713 bp, 922 to 1634) of CAP1 mRNA using RT-PCR and Southern blot using radiolabeled PCR-1.6 as probe. ACT1 mRNA (304 bp) was amplified as a positive control. Lanes 1–4 show strains UnoPP-1, CAC1, CAC1-1A, and CACRE1, respectively.

It is understood that the present invention is not limited to the particular methodology, protocols, cell lines, vectors, and reagents, etc., described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include plural reference unless the context clearly dictates otherwise. Thus, for example, a reference to "a Cap1" is a reference to one or more Cap1's and equivalents thereof known to those skilled in the art and so forth.

Unless defined otherwise, all technical and scientific terms used herein have the same meanings as commonly understood by one of ordinary skill in the art to which this invention belongs. Preferred methods, devices, and materials are described, although any methods and materials similar or equivalent to those described herein can be used in the practice or testing of the present invention. All references cited herein are incorporated by reference herein in their entirety.

Definitions

Homologue: refers to chromosomes carrying the same genetic loci. Thus, a diploid cell has two copies of each homologue, one derived from each parent.

Virulent phage mutant: a mutant that is unable to survive in bacterium as a stable prophage component of the bacterial genome.

Morphogenic: as used herein refers to a factor that induces development of particular cell types in a manner that depends on its concentration.

Open reading frame: as defined herein, includes a sequence of nucleotides that contains a series of triplets coding for amino acids without any termination codons. Such a sequence is potentially translatable to protein.

Promoter: a recognition site on a DNA sequence or group of DNA sequences that provide an expression control element for a gene and to which RNA polymerase specifically binds and initiates RNA synthesis (transcription) of that gene.

Inducible promoter: a promoter where the rate of RNA polymerase binding and initiation is modulated by external stimuli. Such stimuli include light, heat, anaerobic stress, alteration in nutrient conditions, presence or absence of a metabolite, presence of a ligand, microbial attack, wounding and the like.

Viral promoter: a promoter with a DNA sequence substantially similar to the promoter found at the 5' end of a viral gene. A typical viral promoter is found at the 5' end of the gene coding for the p2I protein of MMTV described by Huang et al., 27(2 Pt. 1) Cell 245–55 (1981).

Synthetic promoter: a promoter that was chemically synthesized rather than biologically derived. Usually synthetic promoters incorporate sequence changes that optimize the efficiency of RNA polymerase initiation.

Constitutive promoter: a promoter where the rate of RNA polymerase binding and initiation is approximately constant and relatively independent of external stimuli.

Heterologous Polypeptide: a linear series of amino acid residues connected one to the other by peptide bonds between the alpha-amino and carboxy groups of adjacent residues originating from a species other than the plant host system within which said linear series is produced. "Polypeptide" also encompasses a sequence of amino acids, peptides, fragments of polypeptides, proteins, globular proteins, glycoproteins, and fragments of these.

Multimeric protein: a protein containing more than one separate polypeptide or protein chain, each associated with the other to form a single protein. Both heterodimeric and homodimeric proteins are multimeric proteins.

Immunoglobulin: a polypeptide, protein or multimeric protein containing at least the immunologically active portion of an immunoglobulin heavy chain and is thus capable of specifically combining with an antigen. Exemplary immunoglobulins are immunoglobulin heavy chains, immunoglobulin molecules, substantially intact immunoglobulin molecules, any portion of an immunoglobulin that contains the paratope, including those portions known in the art as Fab fragments, Fab' fragment, F(ab').sub.2 fragment and Fv fragment.

Recombinant: as used herein, broadly describes various technologies whereby genes can be cloned, DNA can be sequenced, and protein products can be produced. As used herein, the term also describes proteins that have been produced following the transfer of genes into the cells of host systems.

Fusion protein: a protein in which peptide sequences from different proteins are covalently linked together.

Hybridization: broadly defined, any process by which a nucleic acid sequence binds to a complementary sequence through base pairing. Hybridization conditions can be defined by, for example, the concentrations of salt or formamide in the prehybridization and hybridization solutions, or by the hybridization temperature, and are well known in the art. Hybridization can occur under conditions of various stringency. In particular, stringency can be increased by reducing the concentration of salt, increasing the concentration of formamide, or raising the hybridization temperature. For example, hybridization under high stringency conditions could occur in about 50% formamide at about 37° C. to 42° C. Hybridization could occur under reduced stringency conditions in about 35% to 25% formamide at about 30° C. to 35° C. In particular, hybridization could occur under high stringency conditions at 42° C. in 50% formamide, 5 times SSPE, 0.3% SDS, and 200 μg/ml sheared and denatured salmon sperm DNA. Hybridization could occur under reduced stringency conditions as described above, but in 35% formamide at a reduced temperature of 35° C. The temperature range corresponding to a particular level of stringency can be further narrowed by calculating the purine to pyrimidine ratio of the nucleic acid of interest and adjusting the temperature accordingly. To remove nonspecific signals, blots can be sequentially washed, for example, at room temperature under increasingly stringent conditions of up to 0.1×saline sodium citrate and 0.5% sodium dodecyl sulfate. Variations on the above ranges and conditions are well known in the art.

Isolated: as used herein, refers to any element or compound separated not only from other elements or compounds that are present in the natural source of the element or compound, but also from other elements or compounds and, as used herein, preferably refers to an element or compound found in the presence of (if anything) only a solvent, buffer, ion, or other component normally present in a solution of the same.

Nucleic acid sequences: as the term is used herein, nucleic acid sequences encoding a CAP1 gene or functional equivalent thereof including those with deletions, insertions, or substitutions of different nucleotides resulting in a polynucleotide that encodes a Cap1 or a functionally equivalent of Cap1. Included within this definition are polymorphisms which may or may not be readily detectable using a particular oligonucleotide probe of the polynucleotide encoding a protein and improper or unexpected hybridization to alleles, with a locus other than the normal chromosomal locus for the polynucleotide sequence encoding a heterologous polypeptide. The encoded protein may also be "altered" and contain deletions, insertions, or substitutions of amino acid residues which produce a silent change and result in a functionally equivalent protein. Deliberate amino acid substitutions may be made on the basis of similarity in polarity, charge, solubility, hydrophobicity, hydrophilicity, and/or the amphipathic nature of the residues as long as the biological or immunological activity of a protein is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine, glycine and alanine, asparagine and glutamine, serine and threonine, and phenylalanine and tyrosine.

The term "nucleic acid sequence," includes an oligonucleotide, nucleotide, or polynucleotide, and fragments thereof, and to DNA or RNA of genomic or synthetic origin which may be single- or double-stranded, and represent the sense or antisense strand, to peptide nucleic acid (PNA), or to any DNA-like or RNA-like material, natural or synthetic in origin.

Antisense gene: an antisense gene is constructed by reversing the orientation of the gene with respect to its promoter so that the antisense strand is transcribed.

Antisense RNA: an RNA molecule complementary to a particular RNA transcript that can hybridize to the transcript and block its function.

Amino acid sequences: as used herein, this term includes an oligopeptide, peptide, polypeptide, or protein sequence, and fragment thereof, and to naturally occurring or synthetic molecules.

Fragments: include any portion of a heterologous peptide or nucleic acid sequence. Heterologous peptide fragments retain at least one structural or functional characteristic of the subject heterologous polypeptides. Nucleic acid sequence fragments are greater than about 60 nucleotides in length, and most preferably includes fragments that are at least about 100 nucleotides, at least about 1000 nucleotides, and at least about 10,000 nucleotides in length.

Chemical derivative: as used herein, a molecule is said to be a "chemical derivative" of another molecule when it contains additional chemical moieties not normally a part of the molecule. Such moieties can improve the molecule's solubility, absorption, biological half-life, and the like. The moieties can alternatively decrease the toxicity of the molecule, eliminate or attenuate any undesirable side effect of the molecule, and the like.

Complementary or complementarity: as used herein, include the natural binding of polynucleotides under permissive salt and temperature conditions by base-pairing. For example, the sequence "A-G-T" binds to the complementary sequence "T-C-A."

Complementarity between two single-stranded molecules may be "partial," in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, which depend upon binding between nucleic acids strands and in the design and use of molecules.

Deletion: as used herein, refers to a change in the amino acid or nucleotide sequence and results in the absence of one or more amino acid residues or nucleotides.

Insertion or addition: as used herein, includes a change in an amino acid or nucleotide sequence resulting in the addition of one or more amino acid residues or nucleotides, respectively, as compared to the naturally occurring molecule.

Introduction: insertion of a nucleic acid sequence into a cell, by methods including infection, transfection, transformation or transduction.

Transfection: as used herein includes the process of introducing a DNA expression vector into a cell. Various methods of transfection are possible including microinjection or lipofection.

Transformation: a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the type of host cell being transformed and may include, but is not limited to, viral infection, electroporation, heat shock, and lipofection.

Functional equivalent: a protein or nucleic acid molecule that possesses functional or structural characteristics that are substantially similar to a heterologous protein, polypeptide, enzyme, or nucleic acid. A functional equivalent of a protein may contain modifications depending on the necessity of such modifications for the performance of a specific function. The term "functional equivalent" is intended to include the "fragments," "mutants," "hybrids," "variants," "analogs," or "chemical derivatives" of a molecule.

Variant: an amino acid sequence that is altered by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Analogous minor variations may also include amino acid deletions or insertions, or both. Guidance in determining which amino acid residues may be substituted, inserted, or deleted may be found using computer programs well known in the art, for example, DNASTAR® software.

% similarity or % identity: refer to the percentage of sequence similarity or identity found in a comparison of two or more amino acid or nucleic acid sequences. Percent similarity can be determined by methods well-known in the art. For example, percent similarity between amino acid sequences can be calculated using the clustal method. See, e.g., Higgins & Sharp, 73 Gene 237–44 (1988). The clustal algorithm groups sequences into clusters by examining the distances between all pairs. The clusters are aligned pairwise and then in groups. The percentage similarity between two amino acid sequences, e.g., sequence A and sequence B, is calculated by dividing the length of sequence A, minus the number of gap residues in sequence A, minus the number of gap residues in sequence B, into the sum of the residue matches between sequence A and sequence B, times one hundred. Gaps of low or of no homology between the two amino acid sequences are not included in determining percentage similarity. Percent similarity can be calculated by other methods known in the art, for example, by varying hybridization conditions, and can be calculated electronically using programs such as the MEGALIGN™ program (DNASTAR Inc., Madison, Wis.).

Operably linked: as used herein, refers to the state of any compound, including but not limited to deoxyribonucleic acid, when such compound is functionally linked to any promoter. In the context of the present invention, the nucleic acid sequence is one that encodes for a Cap1. The promoter sequence initiates and mediates transcription of the nucleic acid sequence.

Vector: a cloning vector that is designed so that a coding nucleic acid sequence inserted at a particular site will be transcribed and translated. A typical expression vector may contain a promoter, selection marker, nucleic acids encoding signal sequences, and regulatory sequences, e.g., polyadenylation sites, 5'-untranslated regions, and 3'-untranslated regions, termination sites, and enhancers. "Vectors" include viral derived vectors, bacterial derived vectors, plant derived vectors and insect derived vectors.

Protein purification: broadly defined, any process by which proteins are separated from other elements or compounds on the basis of charge, molecular size, or binding affinity.

Substantially purified: as used herein, includes nucleic or amino acid sequences that are removed from their natural environment, isolated or separated, and are at least 60% free, preferably at least 75% free, and most preferably at least 90% free from other components with which they are naturally associated.

Expression cassette: is conventional and refers to a combination of regulatory elements that are required by the host for the correct transcription and translation (expression) of the genetic information contained in the expression cassette.

These regulatory elements comprise a suitable (i.e., functional in the selected host) transcription promoter and a suitable transcription termination sequence.

Promoter: generally includes a regulatory region of DNA capable of initiating, directing and mediating the transcription of a nucleic acid sequence. Promoters may additionally comprise recognition sequences, such as upstream or downstream promoter elements, which may influence the transcription rate. Preferably, in the context of the present invention, the promoters are CAP1 gene promoters.

Inhibition: as used herein, refers to a reduction in the parameter being measured, whether it be C. albicans growth or viability. The amount of such reduction is measured relative to a standard (control). "Reduction" is defined herein as a decrease of at least around 25% relative to control, preferably at least around 50%, and most preferably of at least around 75%.

DNA template: refers to double-stranded DNA and where indicated by the particular binding assay to single-stranded DNA that may be negatively supercoiled, possesses a promoter region.

Cis-acting element: refers to a variety of modular elements or target sequences. These elements may be targets for tissue-specific or temporal regulation. Generally, these elements only affect the activity of DNA sequences of its own DNA molecule. These elements may be found within enhancers, promoters, or other regulatory elements of a particular gene.

Microarray: refers to a plurality of polymeric molecules spatially distributed over, and stably associated with, the surface of a substantially planar substrate. The microarray of the present invention refers to a microfabricated array of large numbers of different oligonucleotide probes that can effectively be used to not only detect the presence or absence of target nucleic acid sequences, but to quantify the relative abundance of the target sequences in a complex nucleic acid pool. The oligonucleotide probes are complementary to the RNA transcripts or nucleic acids derived from the RNA transcripts and can quantify the hybridized nucleic acids in the array.

In accordance with the present invention, a patient preferably includes immunocompromised or immunosuppressed humans, for example, those having AIDS or undergoing transplantation or anti-cancer therapy. The invention also preferably relates to humans with primary or secondary immunodeficiencies (see, Merch Manual 16th ed., Chapter 19 (1992), herein incorporated by reference). In addition to mammalian hosts in which the normal immune response has been compromised or suppressed, the invention relates to mammalian hosts in which the normal microbial flora has been disrupted, for example, because of disease (e.g., hereditary, metabolic, infiltrative, or hematologic), trauma (e.g., burn, splenectomy, anesthesia), surgical or clinical procedure (e.g., catheterization or introduction of artificial implants such as dentures), or chemical, radiation, or other immunosuppressive prophylaxis or treatment. Accordingly, the microbial infection of the present invention includes infections related to opportunistic as well as pathogenic microorganisms.

An embodiment of the invention is the expression of the CAP1 gene (SEQ. ID. NO. 2) and the construction of a cap1/cap1 mutant and a CAP1 complemented strain of C. albicans. cap1/cap1 mutants may be generated through the disruption of the CAP1 gene. Thus, the construction of a disruption cassette followed by reiterative site-specific disruption of genomic CAP1 DNA sequences with said disruption cassette resulted in gene inactivation as confirmed by Northern Blotting. Complementation of mutants was achieved through co-transformation with a PCR product containing wild type CAP1 DNA. CAP1 disruption was confirmed by the absence of CAP1 RNA in cap1/cap1 mutants.

Another embodiment of the present invention is the gene product of the CAP1 gene, Cap1 (SEQ. ID. NO.1). Structural feature of C. albicans Cap1 conform closely to adenylate cyclase associated proteins from other organisms (Field et al., supra; Kawamukai et al., supra; Matviw et al., supra; Vojtek and Cooper, supra; Zelicof et al., 271 J. Biol. Chem. 18243–52 (1996)). Amino- and carboxy-terminal halves rich in alpha-helices and beta-sheets, respectively, separated by a central loop containing a stretch of prolines are typical of CAPs that have two domains with separable functions. The SH3-binding motifs and the conserved actin-binding region at the carboxy terminus may interact with an Abp1 homologue and actin monomers in C. albicans as has been shown for similar regions of S. cerevisiae CAP (Freeman et al., 270 J. Biol. Chem. 5680–5 (1995); Freeman et al., 16 Mol. Cell. Biol. 548–56 (1996); Lila and Drubin, 8 Mol. Biol. Cell. 367–85 (1997); Yu et al., supra). An Abp1 homologue was found in the C. albicans genome. Differences in cAMP responses of the cap1/cap1 mutant compared to isogenic CAP1 strains suggest that Cap1 regulates adenylate cyclase activity. cAMP or its membrane permeable derivative, dbcAMP, partially restored filamentation and enhanced hyphae production of the cap1/CAP1 mutant strain, further confirming that Cap1 acts through regulation of cAMP levels. CAP1 (SEQ. ID. NO. 2) encodes the adenylate cyclase associated protein (SEQ. ID. NO. 1) of C. albicans.

Increases in cAMP levels under conditions used in the present invention were directly correlated with bud-hypha transitions and were not simply a response to the presence of fresh media. Comparable cultures placed under conditions supporting budding growth did not show cAMP level increases. The results of the present invention agree with earlier reports of increases in cAMP levels prior to and accompanying germ tube formation (Chattaway et al., 123 Gen. Microbiol. 233–40 (1981); Cho et al., 30 J. Med. Vet. Mycol. 35–42 (1992); Niimi et al., supra). In accord with the present invention, cAMP levels are generally found to be low in budding yeasts that are used to induce germ tubes, except for one study (Egidy et al., 13 Exp. Mycol. 428–32 (1989)) that reported basal cAMP levels to be three-fold higher than in the other studies at time zero. However, cAMP levels dropped within 15 minutes to levels that were consistent with time zero values of the other studies prior to rising. Reasons for the differences are unknown, but use of late stationary phase yeasts (96 h) to induce germ tubes might have contributed to the high cAMP levels at time zero.

The ability of the majority of cap1/cap1 mutant cells to produce hyphae upon prolonged incubation in serum is consistent with a role for cAMP in germ tube formation. An increased length of time may be required to accumulate threshold levels of cAMP in cap1/cap1 mutant cells that are unable to generate pulses of cAMP, but are able to generate cAMP at reduced rates independent of Cap1. The existence of mechanisms independent of Cap1 with lesser effects on cAMP levels is shown by the small increase in cAMP in the cap1/cap1 mutant in germ tube induction conditions. Also, cAMP levels in middle logarithmic phase cultures of cap1/cap1 and CAP1 strains were similar indicating that, as is found for S. cerevisiae (Fedor-Chaiken et al., supra), basal levels of cAMP are not under Cap1 control in C. albicans.

Steroid hormones (Kinsman et al., 31 MYCOSES 617–26 (1988)) and unidentified factors of low molecular weight in serum and seminal fluid that promote hyphal formation (Feng et al., 181 J. Bacteriol. 6339–46 (1999); Barlow et al., 82 Pt. 2 J. Gen. Microbiol. 261–72 (1974)) may interact with C. albicans G protein-coupled receptors leading to Cap1 independent cAMP responses in C. albicans. Even cAMP itself which is present in serum at low levels (Kawarabayashi et al., supra) may work in combination with other factors to promote delayed hyphae formation in serum in cap1/cap1 mutant cells. Superior hyphae-inducing properties of serum relative to other conditions have been noted by others (Castilla et al., 10 Cell Signal 713–9 (1998), Feng et al., supra, Lo et al., 90 Cell 939–49 (1997)). Reasons for the formation of hyphae, albeit at low frequencies, upon prolonged incubation in saliva and M199 without serum are also unknown but may reflect cell cycle influences on the bud-hypha transition (Loeb et al., 19 Mol. Cell. Biol. 4019–27 (1999)).

As described in the present invention, the availability of the cap1/cap1 mutant that grows in yeast forms under hypha-inducing conditions clearly showed for the first time that cAMP profoundly affects bud-hypha transitions and filamentous growth in C. albicans. For strains with CAP1 genes, the role of cAMP was difficult to detect because of the filamentous appearance of wild-type colonies. Addition of cAMP or its membrane permeable derivative, dbcAMP, to the cap1/cap1 mutant in agar media promoted growth as filamentous rather than yeast colonies. Filamentous growth of the cap1/cap1 mutant in the presence of dbcAMP was not quite as extensive as for CAP1 strains. Insufficient uptake or rapid degradation of exogenous cAMP or dbcAMP of cap1/cap1 cells might have led to incomplete restoration of filamentous growth. In S. cerevisiae, the ability to take up cAMP is greatly enhanced by the presence of at least one "cam" mutation. Without at least one cam mutation, strains having mutations in the gene encoding adenylate cyclase, CYR1, cannot survive. One of the cam mutations causes a loss of PDE function, whereas the others are uncharacterized (Griffioen, et al., 275 J. Biol. Chem. 1449–56 (2000); Hall et al., 17 EMBO J. 4370–8 (1998)). By analogy with S. cerevisiae, disruption of the C. albicans PDE2 should generate strains with enhanced filamentous growth properties (Kübler et al., supra; Lorenz and Heitmann, supra; Pan and Heitman, supra).

The positive correlation between addition of cAMP and filamentous growth in both S. cerevisiae and C. albicans along with the requirement of CAP for filamentous growth of S. cerevisiae suggests that the cAMP-dependent signaling pathway of S. cerevisiae during pseudohyphal growth is a good working model for the C. albicans cAMP-dependent signaling pathway during bud-hypha transitions. Gpr1-Gpa1 regulation of cAMP signaling may be also conserved in C. albicans. A Gpr1 homologue with 43% identity in the first five transmembrane regions and an overall identity of 19% to S. cerevisiae Gpr1 was found in the C. albicans genome, as was a Gpa2 homologue (CAG99) with overall identity of 43% to S. cerevisiae Gpa2. C. albicans Ras1 is strongly implicated in cAMP signaling by its 50% identity to Ras2 of S. cerevisiae, which interacts with CAP and affects cAMP levels. Importantly the phenotype of ras1/ras1 null mutants of C. albicans is very similar to that of the cap1/cap1 mutant, with defective bud-hypha transitions and filamentous growth in all hypha-inducing conditions investigated including both liquid and solid media containing serum at 37° C. The similarity in phenotypes between C. albicans ras1/ras1 mutants and cap1/cap1 mutants strongly suggests that C. albicans RAS1 acts in the same signal transduction pathways as CAP1, the cAMP-dependent signaling pathway (Feng et al., supra). Phenotypic similarities also potentially connect a recently identified cdc2-related kinase CRK1 (Chen et al., 20 Mol. Cell. Biol. 8696–708 (2000)), to CAP1 and RAS1. Null mutants in the CRK1 gene have a profound defect in hyphal development in all media tested, and express reduced amounts of hypha-specific genes under germ tube inducing conditions. The present invention also describes reduced amounts of HWP1 expression in cap1/cap1 mutants. Crk1 has been reported to be one of the downstream targets of Ras1 in hyphal development of C. albicans. The transcription factors in C. albicans targeted by cAMP V13 signaling are less clear. Crk1 and Ras1$^{V13}$ suppress the defects in hypha production of C. albicans cph1/cph1 efg1/efg1 pointing to the presence of an unknown transcription factor(s) that serves as a downstream target of cAMP signaling. Expression of C. albicans CRK1 gene in S. cerevisiae led to enhanced filamentous growth that was dependent on Flo8, a PKA-dependent transcription factor. But a homologue of Flo8 has not been found in the C. albicans genome. Another part of the cAMP signaling pathway that is poorly understood involves PKA. Unlike cap1/cap1 and ras1/ras1 mutants, defective germ tube formation is not seen at 37° C. on solid media in C. albicans strains lacking TPK2 encoding the catalytic subunit of PKA. Whether additional TPK genes with differing effects on filamentous growth, as is found in S. cerevisiae (Pan and Heitman, supra), are present in C. albicans is unknown. A gene encoding the regulatory subunit of PKA has been identified in the C. albicans genome.

Defects in hypha formation have been reported for a growing list of null mutants in signal transduction pathway genes. However, the media and temperatures that are required to detect the phenotype for most genes are limited compared to the cap1/cap1 mutant. Null mutants devoid of any one of many other signal transduction pathway genes such as COS1, SSK1, mitogen-activated protein kinase (MAPK) genes (CST20, HST7, CEK1, CPH1), have media-conditional deficiencies in filamentous growth. Strains with mutations of both alleles of the MAPK genes are unable to produce filamentous growth in solid Spider media but make normal hyphae in all other solid or liquid media tested (Csank et al., 66 Infect. Immun. 2713–21 (1998); Kohler and Fink, 93 Proc. Natl. Acad. Sci. USA 13223–8 (1996); Liu et al., 266 Science 1723–6 (1994)). The COS1 and SSK1 genes encoding proteins involved in a two-component signaling pathway are required for hyphal development in solid but not in liquid media (Alex et al., 95 Proc. Natl. Acad. Sci. USA 7069–73 (1998); Calera et al., 68 Infect. Immun. 518–25 (2000)). The phenotypes of cap1/cap1 mutant, ras1/ras1 and crk1/crk1 mutants suggests that defective hypha-formation in serum-containing medium at 37° C. provides a means for identifying proteins involved in the cAMP-dependent pathway.

Genetic studies of S. cerevisiae implicate two roles for CAP, one as a positive regulator of cAMP levels and a second role as a cytoskeletal regulator. The N-terminal third of CAP is responsible for binding adenylyl cyclase and thus regulates cAMP levels, while the widely conserved C-terminal domain of CAP has been shown to sequester monomeric actin, decreasing actin incorporation into actin filaments (Freeman et al., 270(10) J. Biol. Chem. 5680–5 (1995); Freeman et al., 16(2) Mol. Cell. Biol. 548–56 (1996)). Additionally, a recent study on Drosophila and yeast oogenesis has demonstrated that CAP also has a role in oocyte polarity. Both in Drosophila and yeast, CAP mutants failed to establish the proper, asymmetric distribution of mRNA determinants with the oocyte (Baum and Perrimon, 10(16) Curr. Biol. 964–73 (2000)).

Although structural features of C. albicans Cap1 predict cytoskeletal interactions, phenotypic analyses indicate that C. albicans Cap1 differs from other CAPs in influencing cytoskeletal functions. None of the phenotypes of cap mutants of S. cerevisiae attributable to the carboxy terminal cytoskeletal-interacting domain of CAP (inability to grow on rich medium, temperature sensitivity, inviability in response to nitrogen starvation and swollen yeast cell morphology) (Field et al., 61 Cell 319–27 (1990)) or those of S. pombe (temperature sensitivity and abnormal cellular morphology) (Kawamukai et al., supra) were found for C. albicans cap1/cap1 mutants. Cap1 is required for normal hyphal development under all conditions examined. However, the ability of cap1/cap1 mutants to form germ tubes after a delay, and correction of the phenotype by exogenous cAMP and dbcAMP indicated that modulation of cAMP levels, and not cytoskeletal interactions, was responsible for the hypha-promoting effect of Cap1 in C. albicans. This result is consistent with studies in S. cerevisiae showing that neither targeting of CAP to actin cortical patches through the SH3 binding domain, nor interaction of CAP with actin monomers is necessary for CAP to transduce cAMP signals (Yu et al., supra; Zelicof et al., supra).

The absence of the growth defects and aberrant budding phenotypes in C. albicans cap1/cap1 mutants compared to S. cerevisiae and S. pombe cap null mutants points to possible differences in Cap protein-actin interactions that may related to the capacity of C. albicans but not the other yeasts to form germ tubes and true hyphae (Field et al., supra; Kawamukai et al., supra). Although related, pseudohyphal formation and true hyphal formation are distinct processes that are characterized both by morphological differences and differences in gene expression patterns in C. albicans. Cap1 may be in part responsible for the morphological differences between germ tubes and pseudohyphae. In S. cerevisiae, the interaction of CAP with actin monomers through the 27 carboxy terminal amino acids (Zelicof et al., supra) may prevent hyperpolarization and accentuated concentration of actin filaments seen in buds of cap null mutants (Baum and Perrimon, supra). However filamentous actin is highly concentrated at the hyphal tip in C. albicans germ tubes and true hyphae (Anderson and Soll, 132 J. Gen. Microbiol. 2035–47 (1986)). Growth from hyphal tips may require weaker interactions between Cap1 and actin in C. albicans compared to S. cerevisiae to facilitate polarized growth during germ tube and hyphae formation. The results suggest that CAP function is not required for cytoskeletal organization in C. albicans as it is in S. cerevisiae.

The mechanism of Cap1-mediated modulation of bud-hypha transitions and filamentous growth is unknown. Studies with S. cerevisiae suggest that the cAMP-dependent pathway causes cells to undergo unipolar budding, a process that, when coupled with elongated growth controlled by the MAPK kinase pathway, produces pseudohyphal cells (Pan and Heitman, supra). Mösch and Fink (145 Genetics 671–84 (1997)) reported that the S. cerevisiae CAP/SRV2 mutant constructed by transposon mutagenesis is defective in pseudohyphal growth and undergoes random budding. These reports prompt the idea the C. albicans Cap1 may function to interrupt processes important for budding, and that interruption of budding processes is required for bud-hypha transitions and filamentous growth.

Phenotypes of cap1/cap1 mutants also differed from C. albicans strains with mutations in a gene that functions in cytoskeletal regulation and is aberrant in both budding and hyphal morphologies (Leberer et al., 7 Curr. Biol. 539–46 (1997)). The lack of a role for C. albicans Cap1 in cytoskeletal organization may represent an important attribute for resisting stresses such as nitrogen limitation. Whereas C. albicans appears similar to S. cerevisiae in employing the RAS/cAMP pathway for producing filamentous growth on SLAD media (Gimeno et al., supra, Pan and Heitman, supra) S. cerevisiae cap mutants are non-viable in limiting nitrogen (Field et al., supra). In contrast, C. albicans cap1/cap1 mutants survive as budding yeasts when nitrogen is limiting.

The divergent phenotypes of cap mutants in S. cerevisiae and S. pombe illustrate that CAP genes play a key role in the variable responses of different fungi to similar environmental conditions. The primary role of CAP1 in C. albicans may be to mediate rapid induction of bud-hypha transitions in response to a variety of environmental conditions, a hallmark of C. albicans growth. The finding that cap1/cap1 mutants are avirulent in a murine model of systemic candidiasis, as described in the present invention, suggests that antifungal strategies interfering with C. albicans CAP1-mediated signaling are important for preventing or inhibiting candidiasis.

The environmental cues that activate bud/hypha signaling cascades are unknown, but historical data strongly suggest that nitrogen regulatory circuits are involved. In many fungi, nitrogen utilization is important not only for the synthesis of essential metabolites, but also for interconversion between growth morphologies that are important for environmental adaptation. Spore germination in Aspergillus and Rhizopus is preferentially induced in poor nitrogen sources such as proline (Weber et al., 55 Phytopath . 262–6 (1965); Yanagita, 26 Arch. Microbiol. 329–44 (1957)). In diploid strains of S. cerevisiae, nitrogen starvation or use of proline as a nitrogen source leads to production of pseudohyphal cells which invade solid agar, and are thought to be necessary for growth in the natural environment (Gimeno et al., 68(6) Cell 1077–90 (1992)). In C. albicans, the use of proline or selected other amino acids induces production of true hyphae, as well as pseudohyphae from yeast forms (Dabrowa et al., 13 Infect. Immun. 830–5 (1976); Holmes et al., 133 J. Gen. Microbiol. 3219–28 (1987); Land et al., 11(5) Infect. Immun. 1014–23 (1975)). Morphologic variation in response to proline is also found in plant pathogenic fungi and is thought to be important for pathogenesis (Kulkarni et al., 5 Exp. Mycol. 148–54 (1981)). Thus morphologic variation that accompanies the use of nitrogen sources is a common feature of fungal growth.

The control of nitrogen supply by prokaryotic and eukaryotic organisms is highly regulated. Fungi are able to utilize an array of compounds as nitrogen sources, and have evolved the capability to express different catabolic enzymes to make nitrogen available to the cell. Nitrogen metabolism regulation has been well studied in S. cerevisiae, Aspergillus nidulans, and Neurospora crassa. When preferred sources of nitrogen such as ammonia, glutamine, and glutamate are not available or are in concentrations too low to support growth, the synthesis of pathway-specific catabolic enzymes and permeases are derepressed (Marzluf, 61(1) Microbiol. Mol. Biol. Rev. 17–21 (1997)). Activating global regulatory genes in Aspergillus (areA; Caddick, Molecular Biology of Filamentous Fungi 141–52 (1992), Kudla et al., 9(5) EMBO J. 1355–64 (1990)), Neurospora (nit-2; Fu et al., 7(5) Mol. Cell. Biol. 1691–6 (1987); Stewart et al., 46(2–3) GENE 291–5 (1986)), Saccharomyces (gln-3; Minehart et al., 11(12) Mol. Cell. Biol. 6216–28 (1991)), and Penicillum (nre; Haas et al., 27(2) Curr. Genet. 150–8 (1995)) have been found that code for GATA-type zinc finger transcription factors which activate specific catabolic genes when preferred nitrogen sources are lacking. These regulatory proteins all have a conserved DNA binding domain which consists of a single $Cys_2/Cys_2$-type zinc finger motif with a central loop of 17 amino acid residues (Marzluf, supra). The amino acid conservation in the DNA binding region is high among the different members of this GATA family. Mutations of conserved residues in the DNA binding domains of NIT2 or AREA lead to complete lack of DNA binding in vitro and are nonfunctional in vivo (Fu et al., 4(11) Mol. Microbiol. 1847–52 (1990)).

Another aspect of the present invention is the identification of new genes that are regulated by CAP1 controls because such genes are likely to be important in virulence. The null mutant of the putative DNA binding protein genes serves as a tool to achieve this goal as well, for identification of genes with low message levels compared to mRNA from cells with the wild-type DNA binding protein gene. A preferred methodology for the identification of new genes is genome-wide expression monitoring (DeRisi et al., 11(1) Curr. Opin. Oncol. 76–9 (1999)). The proven utility of genome wide expression monitoring in revealing previously unidentified genes that are up or down-regulated under any given environmental conditions has been demonstrate. For example, new sporulation-specific genes, and regulatory circuits were identified using genome-wide expression monitoring of the *S. cerevisiae* genome (Cox et al., 15(8) Yeast 703–13 (1999)). Mammalian genes in fibroblasts that are regulated in the presence of serum have also been identified using genome wide expression monitoring with the available but incomplete mammalian genome sequences (Iyer et al., 283(5398) Science 83–7 (1999)). In both cases, unexpected genes were identified underscoring the value of the technique. Similar studies are plausible using the *C. albicans* genome.

Opportunities for proliferation and invasion of mammalian hosts by *C. albicans* are continuing to increase. Because of the loss of the cellular component of the immune system, AIDS patients are susceptible to invasion of submucosal tissue by *C. albicans*. The frequency of candidal infections may also be a result of the prophylactic use of antibacterial drugs used in AIDS patients to minimize other opportunistic infections. Candidal infections increase in severity and recur more frequently as the immunodeficiency progresses. In non-AIDS patients, such as those undergoing organ transplantation, are neutropenic, or have debilitating diseases requiring advanced modalities of life support, mucosal and hematogenously disseminated candidiasis seriously threaten optimal treatment outcomes. While antifungal drugs can be effective, the increasing frequency of resistant strains of *C. albicans*, and the systemic side effects of the drugs prompts exploration of novel strategies to interrupt the sequence of events leading to disease and to expand the repertoire of antifungal drugs. By defining the molecular events leading to bud/hypha transition, and through the identification of new genes that are co-regulated with CAP1 in a putative global regulatory circuit, the present invention relates to new and novel ways to interfere with candidiasis. The long term medical benefit(s) of this study may be the development of alternative or adjunctive therapies based on the knowledge expression of CAP1 genes in *C. albicans*. Furthermore, better understanding of the role of CAP1 in germ tube formation in multiple conditions suggests that antifungal strategies interfering with *C. albicans* Cap1-mediated signaling will be important for preventing or inhibiting candidates.

Recombinant Techniques

The DNA molecules of the present invention may be employed by recombinant techniques. Thus, for example, the DNA molecule sequence may be included in any one of a variety of expression vehicles, in particular vectors or plasmids for expressing such a polypeptide. Such vectors include: chromosomal, nonchromosomal and synthetic DNA sequences, e.g., derivatives of SV40; bacterial plasmids; phage DNA; yeast plasmids; vectors derived from combinations of plasmids and phage DNA; and viral DNA such as vaccinia, adenovirus, fowl pox virus, and pseudorabies. However, any other vector or plasmid may be used as long as they are replicable and viable in the host.

The appropriate DNA sequence may be inserted into the vector by a variety of procedures. In general, the DNA sequence is inserted into an appropriate restriction endonuclease site by procedures known in the art. Such procedures and others are deemed to be within the scope of those skilled in the art.

The DNA sequence in the expression vector may be operatively linked to an appropriate expression control sequence(s) (promoter) to direct mRNA synthesis. As representative examples of such promoters, there may be mentioned: LTR or SV40 promoter, the *E. coli*. lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably may contain a gene to provide a phenotypic trait for selection of transformed host cells such as dihydrofolate reductase or neomycin resistance for eukaryotic cell culture, or such as tetracycline or ampicillin resistance in *E. coli*.

An embodiment of the invention relates to an isolated DNA molecule comprising the nucleotide sequence of the CAP1 gene (SEQ. ID. NO. 2). This nucleotide sequence, or fragments or functional equivalents thereof, may be used to generate recombinant DNA molecules that direct the expression of the polypeptides of the present invention, or functionally active peptides or functional equivalents thereof, in appropriate host cells. Due to the degeneracy of the nucleotide coding sequence, other DNA sequences which encode substantially the same amino acid sequences as depicted, or analogs or fragments thereof, may be used in the practice of the invention for the cloning and expression of such a gene. Such alterations include deletions, additions or substitutions of different nucleotide residues resulting in a sequence that encodes the same or a functionally equivalent gene product. The gene product may contain deletions, additions or substitutions of amino acid residues within the sequence, which result in a silent change thus producing a bioactive product. Such amino acid substitutions may be made on the basis of similarity in polarity, charge, solubility, hydrophobicity, hydrophilicity, the amphipathic nature of the residues involved and/or on the basis of crystallographic data. For example, negatively charged amino acids include aspartic acid and glutamic acid; positively charged amino acids include lysine and arginine; amino acids with uncharged polar head groups having similar hydrophilicity values include the following: leucine, isoleucine, valine; glycine, alanine; asparagine, glutamine; serine, threonine; phenylalanine, tyrosine.

Techniques well known to those skilled in the art for the isolation of DNA, generation of appropriate restriction fragments, construction of clones and libraries, and screening recombinants may be used. For a review of such techniques, see, for example, Sambrook Et Al., Molecular Cloning: A Laboratory Manual, Chapters 1–18, ($2^{nd}$ ed. Cold Spring Harbor Laboratory 1989) (1982), the disclosure of which is hereby incorporated by reference. Also, the 5' untranslated and coding regions of the nucleotide sequence could be altered to improve the translational efficiency of the mRNA. In addition, based on X-ray crystallographic data, sequence alterations could be undertaken to improve protein stability, e.g., introducing disulfide bridges at the appropriate positions, and/or deleting or replacing amino acids that are predicted to cause protein instability. These are only examples of modifications that can be engineered to produce a more active or stable protein, more protein, or even change the substrate specificity of the protein.

The vector containing the appropriate DNA sequence, as well as an appropriate promoter or control sequence, may be employed to transform an appropriate host to permit the host to express the polypeptides of the present invention. Representative examples of appropriate hosts include: bacterial cells, such as *E. coli, Salmonella typhimurium*, Streptomyces; fungal cells, such as yeast; insect cells, such as Drosophila S2 and Spodoptera Sf9; animal cells, such as CHO, COS or Bowes melanoma; adenoviruses; and plant cells. The selection of an appropriate host and appropriate transformation technique is deemed to be within the scope of those skilled in the art.

More particularly, the present invention also includes recombinant constructs comprising one or more of the sequences of the present invention. The constructs may comprise a vector, such as a plasmid or viral vector, into which a sequence of the invention has been inserted, in a forward or reverse orientation. In a preferred aspect of this embodiment, the construct may further comprise regulatory sequences, including, for example, a promoter operably linked to the sequence. Large numbers of suitable vectors and promoters are known to those of skill in the art, and are commercially available. The following vectors are provided by way of example. Bacterial: pQE70, pQE60, pQE-9 (Qiagen), pBS, phagescript, psiX174, pBluescript SK, pBsKS, pNH8a, pNH16a, pNH18a, pNH46a (Stratagene); pTRC99A, pKK223-3, pKK233-3, pDR540, PRIT5 (Pharmacia). Eukaryotic: pWLneo, pSV2cat, pOG44, pXT1, pSG (Stratagene); pSVK3, pBPV, pMSG, PSVL (Pharmacia). However, any other plasmid or vector may be used as long as they are replicable and viable in the host.

In a further embodiment, the present invention relates to host cells containing the above-described construct. The host cell can be a higher eukaryotic cell, such as a mammalian cell, or a lower eukaryotic cell, such as a yeast cell, or the host cell can be a prokaryotic cell, such as a bacterial cell. The host cell preferably may secrete the recombinant protein. Introduction of the construct into the host cell can be effected by calcium phosphate transfection, DEAE-Dextran mediated transfection, or electroporation (Davis Et Al., Basic Methods In Molecular Biology (1986)).

Promoters

Suitable promoter regions can be selected from any desired gene using CAT (chloramphenicol transferase) vectors or other vectors with selectable markers. Two appropriate vectors are pKK232-8 and pCM7. Particular named bacterial promoters include laci, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of skill in the art. The constructs in host cells can be used in a conventional manner to produce the gene product encoded by the recombinant sequence.

Enhancers

Transcription of a DNA encoding the polypeptides of the present invention by higher eukaryotes may be increased by inserting an enhancer sequence into the vector. Enhancers are cis-acting elements of DNA, usually from about 10 to 300 bp, that act on a promoter to increase its transcription. Examples include the SV40 enhancer on the late side of the replication origin (base pair 100 to 270), a cytomegalovirus early promoter enhancer, a polyoma enhancer on the late side of the replication origin, and adenovirus enhancers.

Selectable Markers

Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), alpha factor, acid phosphatase, or heat shock proteins, among others. The heterologous structural sequence is preferably assembled in appropriate phase with translation, initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Expression Vectors

Useful expression vectors for bacterial use may be constructed by inserting a structural DNA sequence encoding a desired protein together with suitable translation, initiation and termination signals in operable reading phase with a functional promoter. The vector may comprise one or more phenotypic selectable markers and an origin of replication to ensure maintenance of the vector and to, if desirable, provide amplification within the host. Suitable prokaryotic hosts for transformation include *E. coli, Bacillus subtilis, Salmonella typhimurium* and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis.). These pBR322 backbone sections are combined with an appropriate promoter and the structural sequence to be expressed.

Following transformation of a suitable host strain and growth of the host strain to an appropriate cell density, the selected promoter may be de-repressed by appropriate means (e.g., temperature shift or chemical induction) and cells may be cultured for an additional period. Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents. Various mammalian cell culture systems can also be employed to express recombinant polypeptides.

Examples of mammalian expression systems include the COS-7 lines of monkey kidney fibroblasts, described by Gluzman and other cell lines capable of expressing a compatible vector, for example, the C127, 3T3, CHO, HeLa and BHK cell lines (Gluzman, 23 Cell, 175 (1981)). Mammalian expression vectors may comprise an origin of replication, a suitable promoter and enhancer, and also any necessary ribosome binding sites, polyadenylation sites, splice donor and acceptor sites, transcriptional termination sequences, and 5' flanking nontranscribed sequences. DNA sequences derived from the SV40 viral genome, for example, SV40 origin, early promoter, enhancer, splice, and polyadenylation sites may be used to provide the required nontranscribed genetic elements.

Microarrays

An embodiment of the present invention is a microarray containing at least one nucleotide sequence or fragment thereof, of the CAP1 gene. Such a microarray may be used to detect presence or absence of Cap1 in a cell in context of a diagnostic kit. A further embodiment of the present invention is the use of a CAP1 gene diagnostic kit in the determination of gene expression level of wild type strains versus mutant strains. The use of microarrays to monitor expression levels of a multiplicity of genes are known to those skilled in the art from references such as U.S. Pat. No. 6,040,138 issued to Affymetrix, Inc., and U.S. Pat. No. 6,004,755 issued to Incyte Pharmaceuticals, Inc., the disclosures of which are incorporated by reference herein in their entirety. For example, primers that hybridize to vector sequences are employed to amplify small genomic inserts that are robotically spotted on membranes to generate mini-arrays. In any given sample, DNA or RNA samples are labeled with a fluorescent dye and then hybridized to a DNA microarray containing hundreds to thousands of DNA sequences. DNA sequences may be selected from cDNA libraries, genomic DNA, or expressed sequence tags (EST). Subsequent spotting or printing onto the matrix is followed by DNA crosslinking to the matrix. The fluorescence intensities of the microarray are analyzed, and these measurements are then used to assess gene expression of a particular gene within the sample.

The substrates with which the probe molecules are stably associated may be fabricated from a variety of materials, including plastics, ceramics, metals, gels, membranes, glasses, and the like. The arrays may be produced according to any convenient methodology, such as preforming the probes and then stably associating them with the surface of the support or growing the probes directly on the support. A number of different array configurations and methods for their production are known to those of skill in the art and disclosed in U.S. Pat. Nos. 5,445,934; 5,532,128; 5,556,752; 5,242,974; 5,384,261; 5,405,783; 5,412,087; 5,424,186; 5,429,807; 5,436,327; 5,472,672; 5,527,681; 5,529,756; 5,545,531; 5,554,501; 5,561,071; 5,571,639; 5,593,839; 5,599,695; 5,624,711; 5,658,734; and 5,700,637; the disclosures of which are herein incorporated by reference. For microarrays requiring the use of cDNA probes, DNA polymerases, possessing reverse transcriptase activity can be used for the first strand cDNA synthesis step. Examples of suitable DNA polymerases include the DNA polymerases derived from organisms selected from the group consisting of a thermophilic bacteria and archaebacteria, retroviruses, yeasts, Neurosporas, Drosophilas, primates and rodents.

Means of detecting labeled sample nucleic acids hybridized to the probes of the microarray are known to those skilled in the art. Thus, for example, visualization of colorimetric label is sufficient whereas detection of radiation (e.g., with photographic film or a solid state detector) is necessary for radioactive labeled probes. Fluorescent labeled nucleic acids may be detected with fluorescent microscopy. The hybridized array is excited with a light source at the excitation wavelength of the particular fluorescent label and the resulting fluorescence at the emission wavelength is detected. Automated fluorescent microscopy systems are described in U.S. Pat. No. 5,143,854, and International PCT Application WO 00/63,442, the disclosures of which are herein incorporated by reference.

One skilled in the art will appreciate that methods for evaluating the hybridization results vary with the nature of the specific probe nucleic acids used as well as the controls provided. In the simplest embodiment, simple quantification of the fluorescence intensity for each probe is determined. This is accomplished simply by measuring probe signal strength at each location on the microarray (e.g., where the label is a fluorescent label, detection of the amount of fluorescence produced by a fixed excitation illumination at each location on the array). Comparison of the absolute intensities of an array hybridized to nucleic acids from a "test" sample with intensities produced by a "control" sample provides a measure of the relative expression of the nucleic acids that hybridize to each of the probes.

The above described gene expression profiles of thousands of genes can now be examined en masse via cDNA and oligonucleotide microarrays (Shalon et al., 46 Pathol. Biol. 107–9 (1998); Lockhart et al., Nucl. Acids Symp. Ser. 11–2 (1998); Schena et al., 16 Trends Biotechnol. 301–306 (1998)). Gene expression profiles in yeast, mammalian cell lines, and disease tissues have recently been studied (Cho et al., 2 Mol. Cell. 65–73 (1997); Schena et al., 93 Proc. Natl. Acad. Sci. USA 10614–9 (1996); Heller et al., 94 Proc. Natl. Acad. Sci. USA 2150–5 (1997); Welford et al., 26 Nucl. Acids Res. 3059–65 (1998)).

Given the high significance of the identification of new genes with potential importance in virulence in an organism where random mutagenesis approaches are not possible, exploration of alternatives other than genome wide expression monitoring are also warranted. Consequently, a "work-around" method that does not require the production of gene-specific probes may be utilized. Primers that hybridize to vector sequences are employed to amplify small genomic inserts that are robotically spotted on membranes to generate mini-arrays. This array method is being used for genome wide expression monitoring in *H. capsulatum*. The null mutant of the CAP1 gene serves as a tool to achieve this goal as well, for identification of genes with low message levels compared to mRNA from cells with the wild-type CAP1 gene. The ideal methodology for the identification of new genes is genome wide expression monitoring. DeRisi & Iyer, 11(1) Curr. Opin. Onol. 76-79 (1999). The proven utility of genome wide expression monitoring in revealing previously unidentified genes that are up or down-regulated under any given environmental conditions has been demonstrated multiple times. For example, new sporulation-specific genes, and regulatory circuits were identified using genome-wide expression monitoring of the S. cerevisiae genome (Cox et al., 15(8) Yeast 703-13 (1999)). Mammalian genes in fibroblasts that are regulated in the presence of serum have also been identified using genome wide expression monitoring with the available but incomplete mammalian genome sequences (Iyer et al., 283(5398) Science 83-87 (1999)). In both cases, unexpected genes were identified underscoring the value of the technique. Similar studies are plausible using the C. albicans genome. The sequence of the C. albicans genome has been completed to five times coverage.

Gene Therapy Another embodiment of the present invention involves the use of gene therapy applications, which will interfere with the transcription of C. albicans CAP1 genes. Gene therapy has been broadly defined as "the correction of a disease phenotype through the introduction of new genetic information into the affected organism" (Roemer et al., 208 Eur. J. Biochem. 211–25 (1992)). Two basic approaches to gene therapy have evolved: (1) ex vivo gene therapy and (2) in vivo gene therapy. In ex vivo gene therapy, cells are removed from a subject and cultured in vitro. A functional replacement gene is introduced into the cells (transfection) in vitro, the modified cells are expanded in culture, and then re-implanted in the subject. These genetically modified, re-implanted cells are reported to secrete detectable levels of the transfected gene product in situ (Miller, 76 Blood 271–8 (1990)) and Selden et al., 317 New Eng. J. Med. 1067–76 (1987)). The development of improved retroviral gene transfer methods (transduction) facilitates the transfer into and subsequent expression of genetic material by somatic cells (Cepko et al., 37 Cell 1053–62 (1984)). Accordingly, retrovirus-mediated gene transfer has been used in clinical trials to mark autologous cells and as a way of treating genetic disease (Rosenberg et al., 323 New Eng. J. Med 570–8 (1990); Anderson, 2 Human Gene Ther. 99–100 (1991)). Several ex vivo gene therapy studies in humans are reported (reviewed in Anderson, 256 Science 808–13 (1992) and Miller, 357 Nature 455–60 (1992)).

In in vivo gene therapy, target cells are not removed from the subject. Rather, the transferred gene is introduced into cells of the recipient organism in situ, that is, within the recipient. In vivo gene therapy has been examined in several animal models (reviewed in Felgner et al., 349 Nature 351–2 (1991)). Publications have reported the feasibility of direct gene transfer in situ into organs and tissues such as muscle (Ferry et al., 88 Proc. Natl. Acad. Sci. 8377–781 (1991); Quantin et al., 89 Proc. Natl. Acad. Sci. USA 2581–4 (1992)), hematopoietic stem cells (Clapp et al., 78 Blood 1132–9 (1991)), the arterial wall (Nabel et al., 244 Science 1342–4 (1989)), the nervous system (Price et al., 84 Proc. Natl. Acad. Sci. USA 156–60 (1987)), and lung (Rosenfeld et al., 252 Science 431–4 (1991)). Direct injection of DNA into skeletal muscle (Wolff et al., 247 Science 1465–8 (1990)), heart muscle (Kitsis et al., 88 Proc. Natl. Acad. Sci. USA 4138–42 (1991)) and injection of DNA-lipid complexes into the vasculature (Lim et al., 83 Circulation 2007–11 (1991); Ledere et al., 90 J. Clin. Invest. 936–44 (1992); Chapman et al., 71 Circ. Res. 27–33 (1992)) also have been reported to yield a detectable expression level of the inserted gene product(s) in vivo.

Gene therapy efforts have been aimed at the identification of various cell types for transformation, including keratinocytes (Morgan et al., 237 Science 1476–9 (1987)); fibroblasts (Palmer et al., 88 Proc. Natl. Acad. Sci. USA 1330–34 (1991); Garver Jr. et al., 237 Science 762–4 (1987); International PCT Application WO 92/15,676); lymphocytes (Reimann et al., 89 J. Immunol. Meth. 93–101 (1986)); myoblasts (Barr et al., 254 Science 1507–9 (1991); Dai et al., 89 Proc. Natl. Acad. Sci. 10892–5 (1992); Roman et al., 18 Som. Cell Mol. Gen. 247–58 (1992)); smooth muscle cells (Lynch et al., 89 Proc. Natl. Acand. Sci. USA 1138–42 (1992)); and epithelial cells (Nabel et al., 244 Science 1342–4 (1989); International PCT Application WO 90/06, 997, the contents of which references and patent/patent applications are incorporated herein by reference).

The delivery of an effective dose of a prophylactic or therapeutic agent in situ depends on the efficiency of transfection (or transduction) as well as the number of target cells. Epithelial cell-based gene therapy, in particular, involves a relatively small area available in situ for receiving genetically modified epithelial cells. The delivery of an effective dose of prophylactic or therapeutic agent in situ thus depends upon the total number of implanted epithelial cells.

In one embodiment of the invention, exogenous genetic material (e.g., a cDNA encoding a polypeptide antagonist of the polypeptide, SEQ ID NO. 1, of the present invention) is introduced into a syngeneic host cell ex vivo or in vivo by genetic transfer methods, such as transfection or transduction, to provide a genetically modified host cell. Various expression vectors (i.e., vehicles for facilitating delivery of exogenous genetic material into a target cell) are known to one skilled in the art.

Transfection refers to the insertion of nucleic acid into a mammalian host cell using physical or chemical methods. Several transfection techniques are known to those of ordinary skill in the art including: calcium phosphate DNA co-precipitation (Gene Transfer and Expression Protocols in Methods In Molecular Biology, Vol. 7 (E. J. Murray, ed., Humana Press) (1991)); DEAE-dextran; electroporation; cationic liposome-mediated transfection; and tungsten particle-facilitated microparticle bombardment (Johnston, 346 Nature 776–7 (1990)). Strontium phosphate DNA co-precipitation (Brash et al., 7 Mol. Cell. Biol. 2031–4 (1987)) is a preferred transfection method.

In contrast, transduction refers to the process of transferring nucleic acid into a cell using a DNA or RNA virus. A RNA virus (i.e., a retrovirus) for transferring a nucleic acid into a cell is referred to herein as a transducing chimeric retrovirus. Exogenous genetic material contained within the retrovirus is incorporated into the genome of the transduced host cell. A host cell that has been transduced with a chimeric DNA virus (e.g., an adenovirus carrying a cDNA encoding a therapeutic agent) will not have the exogenous genetic material incorporated into its genome, but will be capable of expressing the exogenous genetic material that is retained extrachromosomally within the cell.

Typically, the exogenous genetic material includes the heterologous gene (usually in the form of a cDNA comprising the exons coding for the therapeutic protein) together with a promoter to control transcription of the new gene. The promoter characteristically has a specific nucleotide sequence necessary to initiate transcription. Optionally, the exogenous genetic material further includes additional sequences (i.e., enhancers) required to obtain the desired gene transcription activity. For the purpose of this discussion an enhancer is simply any non-translated DNA sequence which works contiguous with the coding sequence to change the basal transcription level dictated by the promoter. Preferably, the exogenous genetic material is introduced into the host cell genome immediately downstream from the promoter so that the promoter and coding sequence are operatively linked so as to permit transcription of the coding sequence. A preferred retroviral expression vector includes an exogenous promoter element to control transcription of the inserted exogenous gene. Such exogenous promoters include both constitutive and inducible promoters.

Naturally-occurring constitutive promoters control the expression of essential cell functions. As a result, a gene under the control of a constitutive promoter is expressed under all conditions of cell growth. Exemplary constitutive promoters include the promoters for the following genes which encode certain constitutive or housekeeping functions: hypoxanthine phosphoribosyl transferase (HPRT), dihydrofolate reductase (DHFR) (Scharfmann et al., 88 Proc. Natl. Acad. Sci . USA 4626–30 (1991)), adenosine deaminase, phosphoglycerol kinase (PGK), pyruvate kinase, phosphoglycerol mutase, the beta-actin promoter (Lai et al., 86 Proc. Natl. Acad. Sci. USA 10006–10 (1989)), and other constitutive promoters known to those of skill in the art. In addition, many viral promoters function constitutively in eukaryotic cells. These include: the early and late promoters of SV40; the long terminal repeats (LTRs) of Moloney Leukemia Virus and other retroviruses; and, the thymidine kinase promoter of Herpes Simplex Virus, among many others. Accordingly, any such constitutive promoters can be used to control transcription of a heterologous gene insert.

Genes that are under the control of inducible promoters are expressed only or to a greater degree, in the presence of an inducing agent, (e.g., transcription under control of the metallothionein promoter is greatly increased in presence of certain metal ions). Inducible promoters include responsive elements (REs) which stimulate transcription when their inducing factors are bound. For example, there are REs for serum factors, steroid hormones, retinoic acid and cyclic AMP. Promoters containing a particular RE can be chosen in order to obtain an inducible response, and in some cases, the RE itself may be attached to a different promoter, thereby conferring inducibility to the recombinant gene. Thus, by selecting the appropriate promoter (constitutive versus inducible; strong versus weak), it is possible to control both the existence and level of expression of a therapeutic agent in the genetically modified host cell. If the gene encoding the prophylactic or therapeutic agent is under the control of an inducible promoter, delivery of the agent in situ is triggered by exposing the genetically modified cell in situ to conditions for permitting transcription of the prophylactic or therapeutic agent, e.g., by intraperitoneal injection of specific inducers of the inducible promoters which control transcription of the agent. For example, in situ expression by genetically modified host cells of a therapeutic agent encoded by a gene under the control of the metallothionein promoter, is enhanced by contacting the genetically modified cells with a solution containing the appropriate (i.e., inducing) metal ions in situ.

Accordingly, the amount of therapeutic agent that is delivered in situ is regulated by controlling such factors as: (1) the nature of the promoter used to direct transcription of the inserted gene (i.e., whether the promoter is constitutive or inducible, strong or weak); (2) the number of copies of the exogenous gene that are inserted into the host cell; (3) the number of transduced/transfected host cells that are administered (e.g., implanted) to the patient; (4) the size of the implant (e.g., graft or encapsulated expression system); (5) the number of implants; (6) the length of time the transduced/transfected cells or implants are left in place; and (7) the production rate of the prophylactic or therapeutic agent by the genetically modified host cell. Selection and optimization of these factors for delivery of an effective dose of a particular prophylactic or therapeutic agent is deemed to be within the scope of one of skill in the art, taking into account the above-disclosed factors and the clinical profile of the patient.

In addition to at least one promoter and at least one heterologous nucleic acid encoding the prophylactic or therapeutic agent, the expression vector preferably includes a selection gene, for example, a neomycin resistance gene, for facilitating selection of host cells that have been transfected or transduced with the expression vector. Alternatively, the host cells are transfected with two or more expression vectors, at least one vector containing the gene(s) encoding the prophylactic or therapeutic agent(s), the other vector containing a selection gene. The selection of a suitable promoter, enhancer, selection gene and/or signal sequence is deemed to be within the scope of one skilled in the art.

The prophylactic or therapeutic agent can be targeted for delivery to an extracellular, intracellular or membrane location. If it is desirable for the gene product to be secreted from the host cells, the expression vector is designed to include an appropriate secretion signal sequence for secreting the therapeutic gene product from the cell to the extracellular milieu. If it is desirable for the gene product to be retained within the host cell, this secretion signal sequence is omitted. In a similar manner, the expression vector can be constructed to include retention signal sequences for anchoring the prophylactic or therapeutic agent within the host cell plasma membrane. For example, membrane proteins have hydrophobic transmembrane regions that stop translocation of the protein in the membrane and do not allow the protein to be secreted. The construction of an expression vector including signal sequences for targeting a gene product to a particular location is deemed to be within the scope of one of skill in the art.

In an embodiment, vectors for mammalian host cell gene therapy are viruses, more preferably replication-deficient viruses (described in detail below). Exemplary viral vectors are derived from: Harvey Sarcoma virus; ROUS Sarcoma virus; MPSV; Moloney murine leukemia virus; and DNA viruses (e.g., adenovirus) (Temin, *Retrovirus vectors for gene transfer*, in Gene Transfer 149–87 (Kucherlapati, ed., Plenum) (1986)).

Replication-deficient retroviruses are capable of directing synthesis of virion proteins, but are incapable of making infectious particles. Accordingly, these genetically altered retroviral expression vectors have general utility for high-efficiency transduction of genes in cultured cells, and specific utility for use in the method of the present invention. Such retroviruses further have utility for the efficient transduction of genes into host cells in vivo. Retroviruses have been used extensively for transferring genetic material into cells. Standard protocols for producing replication-deficient retroviruses (including the steps of incorporation of exogenous genetic material into a plasmid, transfection of a packaging cell line with plasmid, production of recombinant retroviruses by the packaging cell line, collection of viral particles from tissue culture media, and infection of the target cells with the viral particles) are provided in Kriegler, Gene Transfer and Expression, A Laboratory Manual (W. H. Freeman Co.) (1990) and Murray, E. J., ed., Methods In Molecular Biology, Vol. 7 (Humana Press Inc.) (1991).

The major advantage of using retroviruses for gene therapy is that the viruses insert the gene encoding the therapeutic agent into the host cell genome, thereby permitting the exogenous genetic material to be passed on to the progeny of the cell when it divides. In addition, gene promoter sequences in the LTR region have been reported to enhance expression of an inserted coding sequence in a variety of cell types (see e.g., Hilberg et al., 84 Proc. Natl. Acad. Sci. USA 5232–6 (1987); Holland et al., 84 Proc. Natl. Acad. Sci. USA 8662–6 (1987); Valerio et al., 84 Gene 419–27 (1989)). In vivo gene therapy using replication-deficient retroviral vectors to deliver a therapeutically effective amount of a therapeutic agent can be efficacious if the efficiency of transduction is high and/or the number of target cells available for transduction is high.

Yet another viral candidate useful as an expression vector for transformation of mammalian host cells is the adenovirus, a double-stranded DNA virus. The adenovirus is frequently responsible for respiratory tract infections in humans and thus appears to have an avidity for the epithelium of the respiratory tract (Straus, The Aenovirus 451–96 (H. S. Ginsberg, ed., Plenum Press) (1984)). Moreover, the adenovirus is infective in a wide range of cell types, including, for example, muscle and epithelial cells (Larrick et al., Gene Therapy. Application Of Molecular Biology 71–104 (Elsevier Science Publishing Co., Inc.) (1991)). The adenovirus also has been used as an expression vector in muscle cells in vivo (Quantin et al., 89 Proc. Natl. Acad. Sci. USA 2581–4 (1992)).

Like the retrovirus, the adenovirus genome is adaptable for use as an expression vector for gene therapy, i.e., by removing the genetic information that controls production of the virus itself (Rosenfeld et al., 252 Science 431–4 (1991)). Because the adenovirus functions in an extrachromosomal fashion, the recombinant adenovirus does not have the theoretical problem of insertional mutagenesis.

Thus, as will be apparent to one skilled in the art, a variety of suitable viral expression vectors are available for transferring exogenous genetic material into mammalian host cells. The selection of an appropriate expression vector to express an agent for the identification, prevention or treatment of microbial infection amenable to gene replacement therapy and the optimization of the conditions for insertion of the selected expression vector into the cell are within the scope of one of skill in the art without the need for undue experimentation.

In an alternative embodiment, the expression vector is in the form of a plasmid, which is transferred into the target host cells by one of a variety of methods: physical (e.g., microinjection (Capecchi, 22 Cell 479–88 (1980)); electroporation (Andreason et al., 6 Biotechniques 650–60 (1988)); scrape loading, microparticle bombardment (Johnston, 346 Nature 776–7 (1990)); and cellular uptake as a chemical complex (e.g., calcium or strontium co-precipitation, complexation with lipid, complexation with ligand) (Gene Transfer and Expression Protocols in Methods In Molecular Biology, Vol. 7 (E. J. Murray, ed., Humana Press) (1991)). Several commercial products are available for cationic liposome complexation including Lipofectin (Life Technologies, Inc., Gaithersburg, Md.) (Felgner et al., 84 Proc. Natl. Acad. Sci. USA 7413–7 (1987)) and Transfectam™ (ProMega, Madison, Wis.) (Behr et al., 86 Proc. Natl. Acad. Sci. USA 6982–6 (1989); Loeffler et al., 54 J. Neurochem. 1812–5 (1990)). However, the efficiency of transfection by these methods is highly dependent on the nature of the target cell and accordingly, the conditions for optimal transfection of nucleic acids into host cells using the above-mentioned procedures must be optimized. Such optimization is within the scope of one of skill in the art.

In an embodiment, the preparation of genetically modified host cells contains an amount of cells sufficient to deliver a prophylactically or therapeutically effective dose of a disrupted gene of the present invention to the recipient in situ. The determination of an effective dose of the prophylactic or therapeutic agent for a known microbial infection is within the scope of one of skill in the art. Thus, in determining the effective dose, the skilled artisan would consider the condition of the patient, the severity of the condition, as well as the results of clinical studies of the prophylactic or therapeutic agent being administered.

If the genetically modified host cells are not already present in a pharmaceutically acceptable carrier, they are placed in such a carrier prior to administration to the recipient. Such pharmaceutically acceptable carriers include, for example, isotonic saline and other buffers as appropriate to the patient and therapy. The genetically modified cells are administered by, for example, intraperitoneal injecting or implanting the cells or a graft or capsule containing the cells in a host cell-compatible site of the recipient. As used herein, host cell-compatible site refers to a structure, cavity or fluid of the recipient into which the genetically modified cell(s), host cell graft, or encapsulated host cell expression system can be implanted, without triggering adverse physiological consequences. Representative host cell-compatible sites include, for example, the peritoneal, pleural and pericardial cavities. Preferably, the host cell-compatible site communicates with the lymphatic system, thereby enabling delivery of the therapeutic agent to the vascular system.

In one embodiment, the host cell-compatible site may be denuded prior to implanting the cells. Exemplary denuding methods include but are not limited to: (1) injection of distilled water into the site (e.g., the peritoneal cavity) for 20 minutes, followed by scraping off a portion of the epithelial layer; (2) injection of 0.1% buffered trypsin for 20 minutes followed by scraping; (3) removal of epithelial cells by gentle scraping with a cell scraper and (4) touching a piece of Gelfilm (Upjohn, Kalamazoo, Mich.) to the endothelium.

The genetically modified host cells are implanted in a host cell-compatible site, alone or in combination with other genetically modified host cells. Thus, the instant invention embraces a method for modifying the epithelial system of a recipient by using a mixture of genetically modified host cells, such that a first modified cell expresses a first prophylactic or therapeutic agent of the present invention and a second modified cell expresses a second prophylactic or therapeutic agent. Other genetically modified cell types (e.g., hepatocytes, smooth muscle cells, fibroblasts, glial cells, mesothelial cells or keratinocytes) can be added, together with the genetically altered epithelial cells, to produce expression of a complex set of introduced genes. Moreover, more than one recombinant gene can be introduced into each genetically modified cell on the same or different vectors, thereby allowing the expression of multiple prophylactic or therapeutic agents of the present invention by a single cell.

The instant invention further embraces an epithelial cell graft. The graft may comprise a plurality of the above-described genetically modified cells attached to a support that is suitable for implantation into a mammalian recipient, preferably into the oral cavity. The support can be formed of a natural or synthetic material. According to another aspect of the invention, an encapsulated host cell expression system is provided. The encapsulated system includes a capsule suitable for implantation into a mammalian recipient and a plurality of the above-described genetically modified host cells contained therein. The capsule can be formed of a synthetic or naturally-occurring material. The formulation of such capsules is known to one of ordinary skill in the art. In contrast to the host cells that are directly implanted into the mammalian recipient (i.e., implanted in a manner such that the genetically modified cells are in direct physical contact with the host cell-compatible site), the encapsulated cells may remain isolated (i.e., not in direct physical contact with the site) following implantation. Thus, the encapsulated host cell system is not limited to a capsule including genetically-modified non-immortalized host cells, but may contain genetically modified immortalized host cells.

Polypeptides

As used herein, polypeptide refers to a linear series of amino acid residues connected to one another by peptide bonds between the alpha-amino groups and carboxy groups of adjacent amino acid residues. Additional covalent bonds between portions of the peptide are also present to restrain the conformation of the molecule, such as amide and disulfide bonds. When used herein, protein also refers to a linear series of amino acid residues connected one to the other as in a peptide. The term synthetic peptide means a chemically derived chain of amino acid residues linked together by peptide bonds that is free of naturally occurring proteins and fragments thereof.

Polypeptides of the present invention may include any analog, fragment or chemical derivative of the polypeptide capable of stimulating increases in cAMP levels which in turn promotes bud-hypha transitions or any analog, fragment or chemical derivation of an inhibitor of the polypeptide capable of stimulating increases in cAMP levels which in turn promotes bud-hypha transitions. Polypeptides thus may include soluble peptides, Ig-tailed fusion peptides, members of random peptide libraries (see, e.g., Lam et al., 354 Nature 82–4 (1991); Houghten et al., 354 Nature 84–6 (1991)), combinatorial chemistry-derived molecular library made of D- and/or L-configuration amino acids, and phosphopeptides (including members of random or partially degenerate, directed phosphopeptide libraries, see, e.g., Songyang et al., 72 Cell 767–78(1993)).

Such polypeptides may include those derived from the transcription and translation of the CAP1 gene (SEQ. ID. NO.2) and those derived from the C. albicans Cap1 (SEQ. ID. NO. 1). The term analog refers to any polypeptide having an amino acid sequence, in comparison to the amino acid sequences of the polypeptides of the present invention, in which one or more amino acids have been substituted with other amino acids; where the substituted amino acids allow or require the polypeptide to assume the equilibrium conformation of the domain of the parent protein. Often, cysteine, lysine and glutamic acid will be used for their side chains which can form covalent linkages to restrict the conformation of a peptide.

The term analog shall also include any polypeptide which has one or more amino acids deleted from or added to an amino acid sequence of the C. albicans Cap1, but which still retains stimulatory activity in increasing cAMP levels in the cAMP-PKA signaling pathway. The term fragment includes any portion of an amino acid sequence which retains at least one structural or functional characteristic of the subject C. albicans Cap1, wherein the fragment is capable of stimulating increases in cAMP levels which in turn promote bud-hypba transitions. Any polypeptide or fragment which has one or more amino acids deleted from or added to an amino acid sequence of a C. albicans Cap1 antagonist which inhibits stimulatory activity in increasing cAMP levels in the cAMP-PKA signaling pathway is also included.

The polypeptides of the present invention may be prepared by any known techniques. Conveniently, the polypeptides may be prepared using the solid-phase synthetic technique initially described by Merrifield (15 J. Am. Chem. Soc. 2149–54 (1963)). Other peptide synthesis techniques may be found, for example, in Bodanszky et al., Peptide Synthesis ($2^{nd}$ ed. John Wiley & Sons) (1976) as well as in other reference works known to those skilled in the art. A summary of peptide synthesis techniques may be found in Stuart and Young, Solid Phase Peptide Synthelia (Pierce Chemical Co.) (1984). The synthesis of peptides by solution methods may also be used, as described in The Proteins 105–237 (H. Heurath et al., eds., $3^{rd}$ ed., Vol. 11, Academic Press) (1976). Appropriate protective groups for use in such syntheses will be found in the above referenced texts as well as in McOmie, Protective Groups In Organic Chemistry (Plenum Press) (1973). In general, these synthetic methods involve the sequential addition of one or more amino acid residues or suitably protected amino acid residues to a growing peptide chain. Normally, either the amino or carboxyl group of the first amino acid residue is protected by a suitable, selectively-removable protecting group. A different, selectively-removable protecting group is utilized for amino acids containing a reactive side functional group, such as lysine.

Using solid phase peptide synthesis as an example, the protected or derivatized amino acid is attached to an inert solid support, known as the 'resin,' through its unprotected carboxyl or amino terminus. The majority of known solid phase peptide syntheses are performed with the amino acid carboxyl terminus linked to solid support due to the preponderance of side reactions found with peptide chain extension using amino acids that are N-linked to solid support. In such cases, synthesis would continue with the removal of the N-terminus protecting group of the resin bound amino acid followed by introduction of a suitably protected amino acid under conditions required for amide bond formation. The N-terminus protecting group of the newly formed dipeptide is then removed and the next amino acid (suitably protected) in the sequence added, and so forth. After all the desired amino acids have been linked in the proper sequence, any remaining terminal and side chain protecting group(s) (and solid support) are removed sequentially or concurrently, to provide the final peptide. The polypeptides of the invention preferably are devoid of benzylated or methylbenzylated amino acids. Such protecting group moieties may be used in the course of synthesis, but they are removed before the polypeptides are used. Additional reactions may be necessary, as described elsewhere to form intramolecular linkages to restrain conformation, if desired. The polypeptides of the present invention may also be linked to an additional sequence of amino acids either or both at the N-terminus and at the C-terminus. Such additional amino acid sequences, or linker sequences, can be conveniently affixed to a detectable label, solid matrix, or carrier. Typical amino acid residues used for linking are tyrosine, cysteine, lysine, glutamic acid and aspartic acid, or the like.

Of course, the present polypeptides may also be prepared by recombinant DNA techniques. The present invention also relates to vectors comprising DNA molecules of the present invention, host cells which are genetically engineered with vectors of the invention and the production of polypeptides of the invention by recombinant techniques. Host cells may be genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying genes. The culture conditions, such as temperature, pH and the like, are preferably those previously used with the host cell selected for expression, and will be apparent to the skilled artisan. Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook Et Al., supra.

The polypeptides of the present invention may be recovered and purified from recombinant cell cultures by methods used heretofore, including ammonium sulfate or ethanol precipitation, acid extraction, anion or cation exchange chromatography, phosphocellulose chromatography, hydrophobic interaction chromatography, affinity chromatography, hydroxyapatite chromatography and lectin chromatography. Protein refolding steps can be used, as necessary, in completing configuration of the mature protein. Finally, high performance liquid chromatography (HPLC) can be employed for final purification steps.

The polypeptides of the present invention may be a naturally purified product, or a product of chemical synthetic-procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated with mammalian or other eukaryotic carbohydrates or may be non-glycosylated. Polypeptides of the invention may also include an initial methionine amino acid residue.

Any peptide of the present invention may be used in the form of a pharmaceutically acceptable salt. Suitable acids which are capable of forming salts with the peptides of the present invention include inorganic acids such as hydrochloric acid, hydrobromic acid, perchloric acid, nitric acid, thiocyanic acid, sulfuric acid, phosphoric acid and the like; and organic acids such as formic acid, acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid, and the like.

Suitable bases capable of forming salts with the peptides of the present invention include inorganic bases such as sodium hydroxide, ammonium hydroxide, potassium hydroxide and the like; and organic bases such as mono-, di- and tri-alkyl and aryl amines (e.g., triethylamine, diisopropyl amine, methyl amine, dimethyl amine and the like) and optionally substituted ethanolamines (e.g., ethanolamine, diethanolamine and the like).

Another embodiment of the present invention is the identification and production of a polypeptide antagonist of a polypeptide comprising the amino acid sequence of SEQ. ID No. 1. In this embodiment (1) molecular modeling of the *C. albicans* Cap1 is performed to determine secondary structure and important protein/receptor interactions, (2) a library of polypeptide substrates are designed to mimic the interaction of *C. albicans* Cap1 with its receptor, (3) the substrates are subject to functional assays to determine antagonistic activity, and (4) the most potent antagonist is produced through molecular biology and synthetic methods described in the present invention.

An additional embodiment is the use of plant cell cultures to produce the polypeptide and polypeptide antagonists of the present invention. The employment of plant host systems to produce proteins has been described by Zenk, 30 Phytochem. 3861–63 (1991) and by Goodman, see U.S. Pat. No. 5,550,038. A basic plant vector construct can be employed where the heterologous gene is not readily amenable to detection. Such construct would have a prokaryote selectable marker, preferably suitable for determining if a plant cell has been transformed. A suitable sequence to permit integration of the heterologous sequence into the plant genome is also preferred.

For use in a method of prevention or treatment, such as the prevention or treatment of infection of a mammalian host by a microorganism, the polypeptides of the present invention may be present in a pharmaceutical composition in admixture with a pharmaceutically acceptable sterile vehicle. The pharmaceutical composition may be compounded according to conventional pharmaceutical formulation techniques. In one embodiment, the polypeptide antagonists of the present invention may be used as a vaccine for preventing infection by a microorganism of a mammalian host comprising an effective amount of antagonist against Cap1 in a pharmaceutically acceptable sterile vehicle. In a preferred embodiment, the vaccine is capable of interfering with biochemical signaling pathways of the microorganism with the cells of the host. In another preferred embodiment, the vaccine is capable of interfering with the cAMP-PKA signaling pathways of the microorganism, wherein the cAMP-PKA signaling pathway operates to increase levels of camp in the microorganism.

The vehicle may take a wide variety of forms depending on the form of preparation desired for administration, e.g., sublingual, rectal, nasal, oral or parenteral. Compositions for oral dosage form may include any of the usual pharmaceutical media, such as, for example, water, oils, alcohols, flavoring agents, preservatives, coloring agents and the like in the case of oral liquid preparations (e.g., suspensions, elixirs and solutions) or carriers such as starches, sugars, diluents, granulating agents, lubricants, binders, disintegrating agents and the like in the case of oral solid preparations (e.g., powders, capsules and tablets). Controlled release forms may also be used. Because of their ease in administration, tablets and capsules represent an advantageous oral dosage unit form, in which case solid pharmaceutical carriers may be employed. If desired, tablets may be sugar coated or enteric coated by standard techniques.

For compositions to be administered parenterally, the carrier will usually comprise sterile water, although other ingredients to aid solubility or for preservation purposes may be included. Injectable suspensions may also be prepared, in which case appropriate liquid carriers, suspending agents and the like may be employed. The parenteral routes of administration may be intravenous injection, intramuscular injection or subcutaneous injection.

For intravenous administration, the polypeptides may be dissolved in an appropriate intravenous delivery vehicle containing physiologically compatible substances such as sodium chloride, glycine and the like, having a buffered pH compatible with physiologic conditions. Such intravenous delivery vehicles are known to those skilled in the art.

The polypeptides of the invention may be administered to subjects where alteration of CAP1 gene expression is desired. The peptides may be administered by any convenient means. Oral administration is presently contemplated as a preferred administration route. The amount administered will depend on the activity of the particular compound administered, which may readily be determined by those of ordinary skill in the art.

Antibodies

Antibodies of the present invention may include any polyclonal, monoclonal, humanized, anti-idiotypic, chimeric or single chain antibodies, and FAb, $F(ab')_2$ and FAb expression library fragments, and epitope-binding fragments thereof.

Another embodiment of the present invention relates to a monoclonal antibody to the polypeptide of SEQ ID NO. 1 of the present invention (or an antigenic portion thereof), which may be produced by methods recognized in the art, including the formation of monoclonal antibody-producing hybridomas (Kohler et al., 256 Nature 495–97 (1975); Kohler et al. 6 Eur. J. Immunol. 511–19 (1976)).

The monoclonal antibodies of the present invention can be used as probes in detecting discrete antigens expressed by microorganisms. The expression or lack of expression of these antigens can provide clinically exploitable information that is not apparent after standard histopathological evaluations. It may thus be possible to correlate the immunophenotypes of individual microorganisms with various aspects of microbial-mammalian host interaction and responsiveness to certain types of therapies, thereby establishing important classifications of prognosis.

The antibodies may also be used to detect drug resistance in microorganisms. For example, drug resistant *C. albicans* can make hyphae (germ tubes) in the presence of drug, but susceptible strains cannot (see 138 J. Gen. Microbiol. 1901–11 (1992)). Because CAP1 is a marker of bud/hypha transition, the detection of the presence or absence of CAP1 may be useful in the monitoring of drug resistance in *C. albicans*.

The use of the monoclonal antibodies described herein can be extended to the screening of human biological fluids for the presence of the specific antigenic determinant recognized. In vitro immunoserological evaluation of sera withdrawn from patients thereby permits non-invasive diagnosis of microbial infection. By way of illustration, human fluids, such as pleural fluids or lymph, can be taken from a patient and assayed for the specific epitope, either as released antigen or membrane-bound on cells in the sample fluid, using monoclonal antibodies against the polypeptides of the present invention in standard radioimmunoassays or enzyme-linked immunoassays known in the art or competitive binding enzyme-linked immunoassays.

The monoclonal antibodies of this invention are potentially useful for targeting microbial infection in vivo. They can therefore be used in humans for localization and monitoring of the microbial infection. For this application, it is preferable to use purified monoclonal antibodies. Purification of monoclonal antibodies for human administration by ammonium sulfate or sodium sulfate precipitation followed by dialysis against saline and filtration sterilization has been described by Miller et al. in Hybridomas In Cancer Diagnosis and Therapy 134 (1982).

In an alternate embodiment, the antibodies described herein are used to stimulate the production of corresponding anti-idiotypic antibodies. In brief, anti-idiotypic antibodies, or antiidiotypes are antibodies directed against the antigen combining region or variable region (idiotype) of another antibody. Based on Jerne's network model of idiotypic relationships (Jerne, 125 Ann. Immunol. 373 (1974); Jerne et al., 1 EMBO 234 (1982)), immunization with an antibody molecule expressing a paratope (antigen-combining site) for a given antigen should produce a group of anti-antibodies, some of which share with the antigen a complementary structure to the paratope. Immunization with a subpopulation of antiidiotypic antibodies should in turn produce a subpopulation of antiidiotypic antibodies which bind the initial antigen. Thus, the administration of the monoclonal antibodies of the present invention may result in a modification of the host's anti-microbial immune response, as the consequence of the formation of anti-idiotypic antibodies which may develop during therapy with the monoclonals.

The monoclonal antibodies of this invention can be used in conjunction with a broad spectrum of pharmaceutical or cytotoxic agents that selectively affect a microorganism over the mammalian host. The methods used for binding the cytotoxic agents to the monoclonal antibody molecule can involve either non-covalent or covalent linkages. Since non-covalent bonds are more likely to be broken before the antibody complex reaches the target site, covalent linkages are preferred. For instance, carbodiimide can be used to link carboxy groups of the pharmaceutical agent to amino groups of the antibody molecule. Bifunctional agents such as dialdehydes or imidoesters can be used to link the amino group of a drug to amino groups of the antibody molecule. The Schiff base reaction can be used to link drugs to antibody molecules. This method involves the periodate oxidation of a drug or cytotoxic agent that contains a glycol or hydroxy group, thus forming an aldehyde that is then reacted with the antibody molecule. Attachment occurs via formation of a Schiff base with amino groups of the antibody molecule. Additionally, drugs with reactive sulfhydryl groups have been coupled to antibody molecules.

Another embodiment of the invention relates to a diagnostic kit for detecting a microorganism expressing a protein. The diagnostic kit may further comprise, where necessary, other components of the signal producing system, including agents for reducing background interference, control reagents, or an apparatus, container or other solid support for conducting the test. The binding of antibody to the target can be detected by well known methods, including radiation (e.g., use of a radioactive nucleotide), colorimetry (e.g., use of an enzyme that can cause a color change in a substrate), fluorescence (e.g., use of a dye such as propidium iodide, fluorescein, or rhodamine), and luminescence (e.g., use of an alkaline phosphatase substrate that releases photons upon cleavage or luciferin). Detection can be qualitative or quantitative.

Antisense Compounds

A further embodiment of the present invention involves the use of oligomeric antisense compounds, particularly oligonucleotides, for inhibiting the function of nucleic acid molecules encoding the *C. albicans* Cap1 (SEQ. ID. NO. 1). Antisense technology has successfully inhibited expression of a variety of genes (Agrawal, 10 Trends Biotech. 152 (1992)). These include inhibition of murine and human IL-1-stimulated PGE2 synthesis (Burch and Mahan, 88 J. Clin. Invest. 1190 (1991)), inhibited expression of a mutated human procollagen gene (Colige et al., 32 Biochem. 7 (1993)), and inhibition of mutant Ha-ras mRNA expression (Monia et al., 267 J. Biol. Chem. 19954 (1992)). Hybridization of the antisense compound to one or more of the nucleic acids encoding Cap1 interferes with normal function of the nucleic acid(s). In this case, the mRNA transcribed from the CAP1 gene is targeted. The preferred sites for interference is the region encompassing the translation initiation or termination codon of the open reading frame for the gene.

Antisense oligonucleotides are the preferred form of antisense compounds but oligonucleotide mimetics may also be used. Oligonucleotides are composed of heterocyclic bases and sugars linked by a phosphodiester group. Oligonucleotide mimetics are therefore compounds that retain the basic structure and function of an oligonucleotide but contain modified or novel groups replacing one or more heterocyclic base, sugar or phosphodiester linkage or any combination thereof. Examples of modified nucleobases include synthetic and natural nucleobases such as those described in U.S. Pat. No. 3,687,808, described in The Concise Encyclopedia of Polymer Science and Engineering 858–859 (Kroschwitz ed., John Wiley & Sons) (1990), disclosed by Englisch et al., 30 Angew Chem., Int. Ed., 613 (1991), and disclosed by Sanghvi, Antisense Research and Applications 289–302 (Crooke and Lebleu, eds., CRC Press) (1993). Substituted sugar moieties include 2' substituted OH; F; O-, S-, or N-alkyl; O-, S-, or N-alkenyl; O-, S-, or N-alkynyl; or O-alkyl-O-alkyl among others, as well as 3' substituted sugars of the 3' terminal nucleotide and the 5' substituted sugars of 5' terminal nucleotide. Examples of modified backbones or non-natural internucleoside linkages include phosphorothioates, chiral phosphorothioates, phosphorodithioates, phosphotriesters, aminoalkylphosphotriesters, methyl and other alkyl phosphonates, chiral phosphonates, phosphinates, phosphoramidates, aminoalkylphosphoramidates, thionophosphoramidates, thiono-alkylphosphonates, thionoalkylphosphotriesters, and boranophosphates. Peptide nucleic acids (PNA) which replace both the sugar and the internucleoside linkage may also be used as oligonucleotide mimetics (Nielsen et al., 254 Science, 1497–1500 (1991)).

The invention has been disclosed broadly and illustrated in reference to representative embodiments described above. Those skilled in the art will recognize that various modifications can be made to the present invention without departing from the spirit and scope thereof.

Without further elaboration, it is believed that one skilled in the art, using the preceding description, can utilize the present invention to the fullest extent. The following examples are illustrative only, and not limiting of the remainder of the disclosure in any way whatsoever.

EXAMPLES

Example 1

C. albicans Strains and Growth Conditions

The E. coli strain HB101 was used to propagate plasmids (Boyer et al., 41 J. Mol. Biol. 459–72 (1969)). C. albicans strains are listed in FIG. 1. Yeast forms were grown in yeast extract peptone dextrose (YPD) or yeast nitrogen base containing 50 mM glucose (YNB) (Rose et al., Methods In Yeast Genetics (Cold Spring Harbor Laboratory Press) (1990)). Mass conversion of stationary phase yeasts (grown at 30° C. for 48 h) to germ tubes was induced at 37° C. in the following pre-warned media, Lee's media (pH 6.8) (Lee et al., 13 Sabouradia 148–53 (1975)), Medium 199 (Gibco-BRL) with 150 mM HEPES (pH 7.0) (M199), M199 containing 5% bovine calf serum (Sigma) (M199+serum), 50 mM potassium phosphate (pH 6.0) plus 10% bovine calf serum (Feng et al., supra), 10 mM imidazole-HCl buffer media (pH 7.0) containing 0.2 mM $MnCl_2$ with the following inducing agents: 1) 4 mM N-acetylglucosamine, 2) 10 mM L-proline plus 10 mM glucose, and 3) 2.5 mM glutamine plus 2.5 mM glucose (Shepard et al., 26 Can. J. Microbiol. 21–6 (1980), Dabrowa, et al., 127 J. Gen. Microbiol. 391–7 (1981)). Whole human saliva was collected on ice and clarified by centrifugation at 10,000×g for 15 min at 4° C. (Kimura et al., 21 Infect. Immun. 64–8 (1978)). Tetracycline was added to clarified saliva at a concentration of 50 μg/ml to inhibit bacterial growth.

For growth analysis in agar-containing media, stationary phase yeasts were mixed (100 cells/20 ml media) with liquified agar containing, M199 adjusted to neutral pH with 7.5% sodium bicarbonate, Spider medium (Liu et al., 266 Science 1723–6 (1994)), 2% agar containing 4% bovine calf serum (Lo et al., 90 Cell 939–49 (1997)), and synthetic low ammonium dextrose (SLAD) containing 50 μM ammonium sulfate (Csank et al., 66 Infect. Immun. 2713–21 (1998)). Filamentous growth on YPD agar was assessed by streaking strains on YPD plates followed by incubation at room temperature for two weeks. Each plate was examined daily for the presence of filamentous growth.

To determine the effect of exogenous cAMP on bud-hypha transitions and filamentous growth of cap1/cap1 mutants, stationary phase yeasts were induced to form germ tubes and hyphae in liquid M199+serum ($10^6$ cells/ml) or in SLAD agar plates containing 10 mM cAMP or dbcAMP (Sigma). M199+serum containing cAMP or dbcAMP were incubated at 37° C. for 20 h and the frequency of germ tube formation was measured at various time points. SLAD plates containing cAMP or dbcAMP were incubated at 37° C. for 5 days, and filamentous growth was monitored daily.

Example 2

Isolation and DNA Sequencing of cDNA and Genomic Clones for CAP1

CAP1 cDNA clones were found while attempting to identify germ tube-specific surface antigens by screening a C. albicans germ tube cDNA library (Sundstrom et al., 174 J. Bacteriol. 6789–99 (1992)) but cDNAs encoding cell wall surface proteins were not found. Five of the thirteen cDNA clones isolated encoded proteins with homology to adenylate cyclase associated proteins. pBluescript SK-phagemids of the five clones were rescued by in vivo excision (Strategene) according the manufacturer's directions. pCAP1, with a 1655 bp CAP1 cDNA insert was analyzed further.

Three X genomic CAP1 clones (CAP2, CAP3, and CAP5) were isolated by screening a λGEM12 genomic library of C. albicans SC5314 (Birse et al., 61 Infect. Immun. 3648–55 (1993)) with CAP1 cDNA excised from pCAP1 with XbaI and XhoI. pGHCP17 was constructed by subcloning the 3.7 kbp CAP1 genomic HindIII fragment of CAP5 into pBluescript SK- and transforming E. coli HB101 (Boyer et al., 41 J. Mol. Biol. 459–72 (1969)). DNA sequences of cDNA and genomic clones were determined by automated cycle sequencing using an automated DNA sequencer (ABI Prism, model 377 and 373, Perkin-Elmer Co.).

Complete genomic DNA sequence of CAP1 was compared with the sequence of SR V2 in the current assembly 6 of the C. albicans genomic sequences from the Stanford DNA Sequencing and Technology Center website at http://www.sequence.stanford.edu/group/candida.

Example 3

Disruption of CAP1

To disrupt CAP1 in C. albicans, plasmid pCAPURA3 was constructed by replacing 132 bp StyI-BsmI fragment of CAP1 cDNA in pCAP1 with the 4.0 kbp BamHI-BglII hisG-URA3-hisG cassette from p5921 (Fonzi et al., 134 Genetics 717–28 (1993)) after generating blunt ends using T4 DNA polymerase (Gibco-BRL) and the Klenow fragment of E. coli DNA polymerase I. E. coli HB101 served as the host strain for transformation and propagation of pCAPURA3.

CAI4 (CAP1/CAP1, ura3/ura3) was transformed using spheroplast transformation (Kurtz et al., 6 Mol. Cell. Biol. 142–9 (1986)) with 10 μg of pCAPURA3 digested with PstI to release the CAP1 disruption cassette. Ura+ transformants with an CAP1/cap1::hisG-URA3-hisG genotype were identified by Southern blotting using HindIII-digested genomic DNA (Scherer et al., 25 J. Clin. Microbiol. 675–9 (1987)). Southern blots were probed with hisG-URA3-hisG from p5921 and PCR-1.2 (FIG. 2A). PCR-1.2 (nucleotides 98 to 1318) was generated by PCR using pGHCP17 as template and oligonucleotides CAP-R4 (5'CCATTTTCCAAGA GGAAGCA3') and CAP-F4 (5'CCGACACTGCATT TGCTTTA3'). Probes were labeled using the enhanced chemiluminescence (ECL) Direct Nucleic Acid Labeling and Detection System (Amersham). CAC1-1 (ura3/ura3 CAP1/cap1::hisG) was selected on YNB media (0.002% uridine) containing 0.05% 5-fluoroorotic acid (5-FOA) (Boeke et al., 197 Mol. Gen. Genet. 345–6 (1984)) and used in a second round of transformation to disrupt the remaining copy of CAP1. Colony PCR (van Zeijl et al., 59 J. Biotech. 221–4 (1997)), using the TaqPlus Long PCR system (Stratagene) with primers CAP-R4 and CAP-F4, and Southern blotting were used to determine genotypes. Gene inactivation was confirmed by Northern blot analysis and RT-PCR.

Complementation of cap1/cap1 mutants at the CAP1 genomic locus was accomplished by co-transformation of a ura3 homozygous cap1/cap1 mutant strain, CAC1-1A1 with eno::URA3 (Staab et al., 283 Science 1535–8 (1999)) and PCR-1.2 creating CACRE1. DNA sequencing of genomic DNA clones from CACRE1 confirmed that mutations were not inadvertently introduced from PCR-1.2 into the CAP1 locus in the revertant.

Cell morphologies were examined using a 40×or 20×objective and differential interference contrast microscopy (OLYMPUS BX60) and photographed (OLYMPUS Magnafire, Model S99806). Colonial morphologies were examined using a stereomicroscope (OLYMPUS SZX12) (1.6×objective) with a transmitted light console base or OLYMPUS BX60 microscope (4×objective), and cellular morphologies at colony rims were examined with brightfield illumination using a light microscope (Nikon, LABOPHOT-2)(10×objective) equipped with a CCD video camera system (OPTRONICS). Photographed images were processed using Adobe PhotoShop 2.5.

Northern Blot Analysis.

Total RNA was isolated (Staab et al., 271 J. Biol. Chem. 6298–305 (1996)) from middle logarithmic phase yeast cultured in 250 ml YNB at 27° C. or germ tubes (yeasts for the cap1/cap1 mutant) cultured for three hours in M199 at 37° C. and treated with RNase-free DNase I (Gibo-BRL). Probes were PCR-1.2 (FIG. 2A) and a 687 bp PCR product amplified from the 18S rRNA gene of C. albicans SC5314 (Makimura et al., 40 J. Med. Mircobiol. 358–64 (1994)) using primers (5'-ACTTTCGATGGTAGGATAG-3' and 5'-TGATCATCTTCGATCCCCTA-3'). Electrophoresis, radiolabeling of probes using the random primer method (Feinberg and Vogelstein, 132 Anal. Biochem. 6–13 (1983); Feinberg and Vogelstein 137 (Addendum) Anal. Biochem. 266–7 (1984)), hybridization and molecular size determination were performed as described by Staab et al. (J. Biol. Chem., supra), except that blots were hybridized first with the CAP1 probe ($10^7$ cpm), autoradiographed and then used with the 18S rRNA probe ($10^6$ cpm).

RT-PCR

The first-strand cDNA was synthesized using 1 μg of total RNA according to the manufacturer's directions (Promega; Reverse Transcription System) and was diluted in a final 100 μl volume of nuclease-free water. Two PCR products representing the 5'-(1 to 605) and 3'-(922 to 1634) portions of CAP1 message (FIG. 2A) were amplified from the first-strand cDNA (10 μl) using oligonucleotides CAP-NRT1 (5'-ATGTCAACCGAGGAGAGTCA-3') and CAP-F1(5'-ATGTACGAGATTGGTGTAGG-3') and CAP-R3 (5'-AGTGAAAATCCATCTCCAGC-3') and CAP-3F1 (5'-CCAGCATGTTCAACAATTTGAG-3') respectively. ACT1 cDNA (304 bp), amplified using two ACT1-specfic primers, ACT-3R (5'-GGAGTTGAAAGTGGTTTGGTCAATAC-3') and ACT-5L (5'-GGCTGGTAGAGACTTGA CCAACCATTTG-3') (Naglik et al., 67 Infect. Immun. 2482–90 (1999)) served as a control. PCR products were detected by Southern blotting using PCR-1.6, which spanned the entire CAP1 coding region, as a probe (FIG. 2A) PCR-1.6 (nucleotides 1 to 1634) was generated by PCR using pGHCP17 and oligonucleotides CAP-NRT1 and CAP-3F1. Probe PCR-1.6 was labeled with [α-$^{32}$P]-dCTP (Amersham) as for Northern blot except that 2×$10^6$ cpm was added to the membrane.

Cyclic AMP Assay

Intracellular cAMP levels in M199 was extracted as previously described by Fedor-Chaiken et al., (supra) and measured using the cAMP enzyme immunoassay (Amersham). Strains (UnoPP-1, CAC1, CAC1-1A, and CACRE1) were grown to middle logarithmic phase ($OD_{600nm}$=0.6–0.7) in M199 at 27° C. and then inoculated (4×$10^6$ cells/ml) into M199 prewarmed to 37° C. to induce germ tubes or fresh M199 at 27° C. for budding growth. At each time point during germ tube formation (or budding in the case of the cap1/cap1 mutant), 27 and 1.5 ml portions were withdrawn for measurement of cAMP levels and protein concentration, respectively.

Protein concentrations (Coomassie protein assay, Pierce) were determined on cell extracts from 1.5 ml of culture lysed by boiling of 5 min in 50 μl of 2N NaOH. Bovine serum albumin (5–25 μg/ml) was used to generate a standard curve.

Screening and DNA Sequence Analysis of Genomic CAP1.

C. albicans cDNAs homologous to CAP (also called SR V2) genes were used to isolate three independent genomic clones, each containing a 3.7 kb HindIII fragment (diagramed in FIG. 2A) found in C. albicans genomic DNA (FIG. 2B, lane 1). A gene encoding an open reading frame identical to that found in the cDNA was named CAP1 because of similarities to CAP genes from other organisms as described below. The protein product of CAP1 was designated Cap1. Two, silent, nucleotide difference was found between C. albicans CAP1 and C. albicans SRV2 reported by the Stanford DNA Sequencing and Technology Center (assembly 6).

Figure 3:
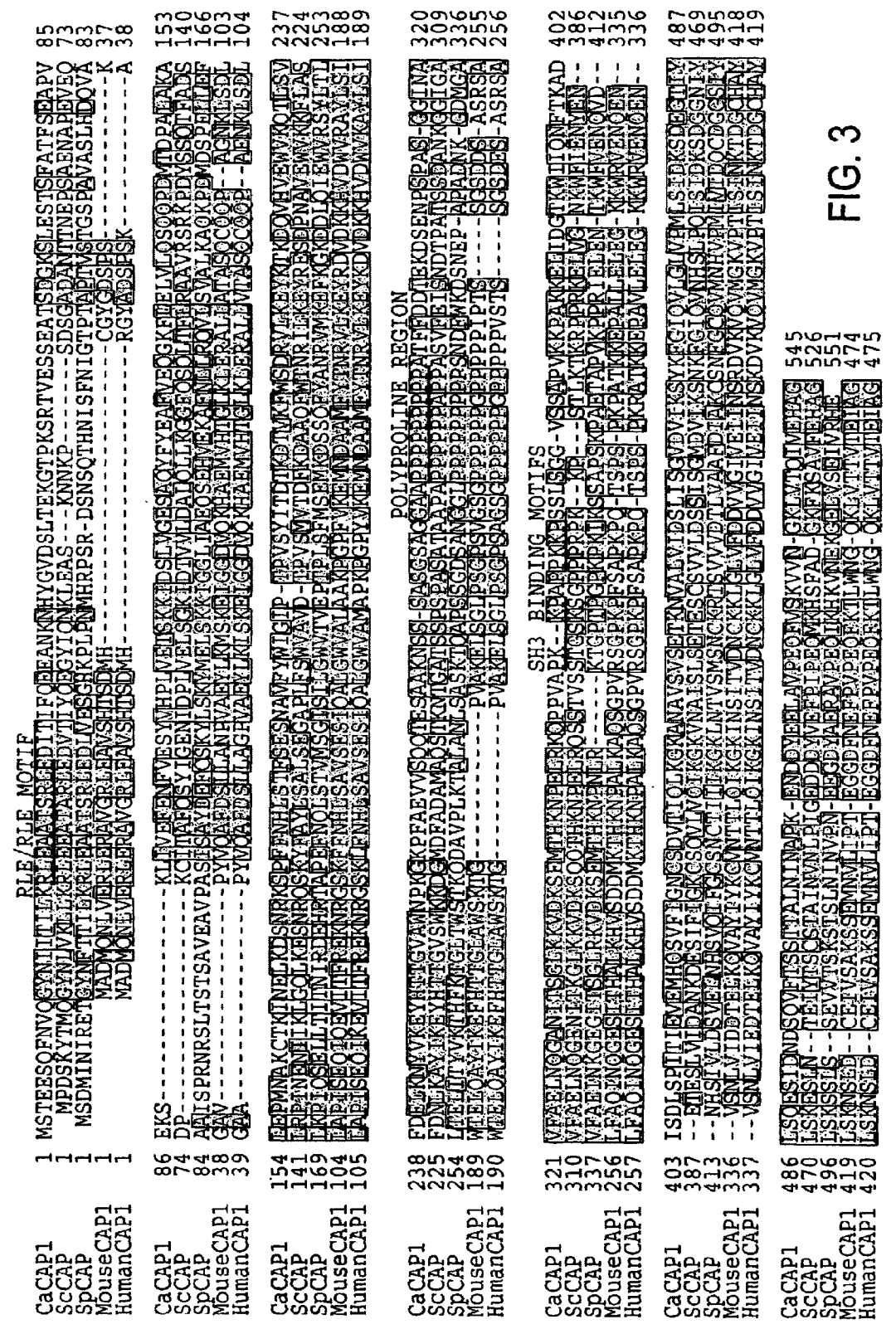

The predicted C. albicans Cap1 was 28–44% identical in overall primary amino acid sequence to CAPs from other organisms. The conserved RLE/RLE motif important for monomer association, protein localization, and Ras/cAMP dependent signaling (Shima et al., 20 Mol. Cell. Biol. 26–33 (2000); Yu et al., supra; Zelicof et al., supra), the universally conserved and centrally-located stretch of proline residues of unknown function, and two consensus SH3-binding motifs (PXXP) were found in C. albicans Cap1 (FIG. 3). Interestingly, the first 100 amino acids of C. albicans Cap1 showed more dissimilarities to CAPs from other organisms than did the remainder of the protein. The first 100 amino acids of C. albicans Cap1 showed only 28.2 and 26.5% identity to the corresponding regions of S. cerevisiae and S. pombe CAPs, respectively, compared with 45.1 and 41.1% identity in carboxy terminal regions, respectively.

Predicted secondary structures of C. albicans Cap1 and CAP of S. cerevisiae were strikingly conserved with amino terminal halves consisting of α-helices separated by loops with small regions of β-sheet and carboxy terminal thirds consisting of β-sheets and loops. The central domain containing prolines was predicted to be a loop in both proteins. Hydrophobicity profiles of the two proteins were also similar (Kyte and Doolittle, 157 J. Mol. Biol. 105–32 (1982)).

Example 4

Expression of the CAP1 Gene

CAP1 was neither a highly expressed nor a developmentally regulated gene (FIG. 4). Detection of the 1.7 kb CAP1 transcript in yeast (FIG. 4A) and germ tube RNA (FIG. 4B) by Northern blotting required lone exposure times. Low mRNA abundance was consistent with unbiased codon usage in that the effective number of codons (Wright, 87 GENE 23–9 (1990)) 43.1, was typical of genes that are expressed at low levels such as PKC1 and MKC1 with values of 45 and 54.8 respectively.

Construction of cap1/cap1 Mutant and CAP1 Complemented Strain of C. albicans.

Reiterative site-specific disruption of genomic CAP1 DNA sequences with hisG-URA3-hisG or hisG produced HindIII fragments of 7.6 and 4.7 kb in size, respectively, that hybridized to probes for CAP1 (FIG. 2B) and hisG-URA3-hisG DNA. To verify that phenotypes of the cap1/cap1 mutant were caused by disruption of CAP1 genes, a complemented strain, CACRE1, was constructed by reintroducing the wild type CAP1 DNA into one of the CAP1:hisG loci of the Ura$^-$ cap1/cap1 mutant using co-transformation (Staab et al., 283 Science 1535–8 (1999)). CAP1 disruption was confirmed by the absence of CAP1 RNA in the cap1/cap1 mutant CAC1-1A in Northern blot analysis (FIGS. 4A and 4B). To show that read-through or truncated CAP1 mRNA was not present in the cap1/cap1 mutant, RT-PCRs were performed using CAP1-specific primers. CAP1 mRNA could not be detected using a probe (PCR-1.6) which spans the entire coding region of CAP1 (FIG. 4C). Equivalent levels of ACT1 cDNA (304 bp) were present in all strains (FIG. 4C). The cap1/cap1 mutant does not have CAP1 mRNA and cannot produce full or truncated Cap1 proteins.

Analysis of cap1/cap1 Mutants.

Growth rates of the cap1/cap1 mutant were equivalent to that of the other strains in rich media (YPD) but were reduced in minimal media (YNB) (FIG. 5). Budding appeared morphologically normal in both media.

Figure 6A:
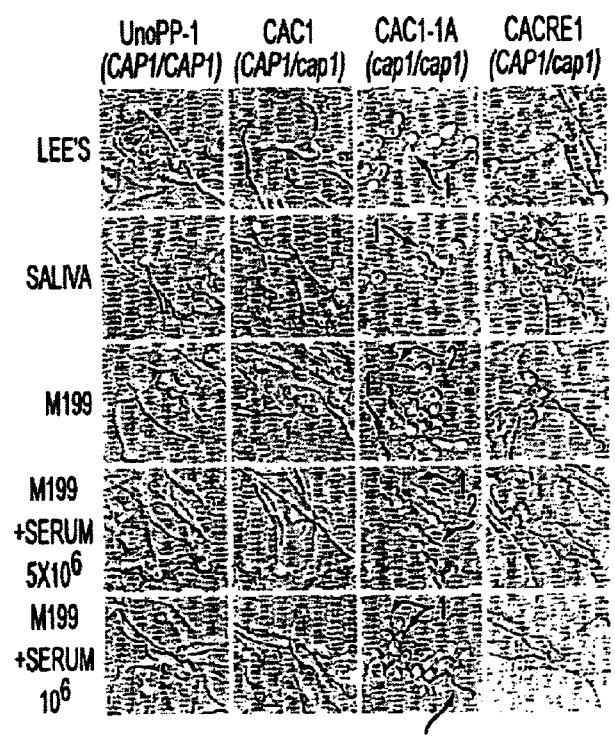
FIGS. 6A–6B depict the phenotypic analyses of cap1/cap1 mutants in liquid media. cap1/cap1 strains were defective in bud-hypha transitions. Germ tubes were induced at cell concentrations of $5 \times 10^6$ cells/ml (first four rows in FIGS. 6A and 6B) of $1 \times 10^6$ cells/ml (bottom row) in prewarmed Lee's media, saliva, M199, or M199+serum for 5 and 20 h. cap1/cap1 mutant cells formed buds (arrows "1") or pseudohyphae at low frequency (arrows "2") whereas strains having CAP1 (UnoPP-1, CAC1, and CACRE1) produced typical germ tubes (first two and fourth columns in FIGS. 6A and 6B). At 20 h a few cap1/cap1 mutant yeasts (<10%) produced germ tubes in saliva or M199 (arrows "3"). In the presence of serum the frequency of germ tube formation was higher (20–30%) (arrow "4"). Reducing the inoculum concentration in the presence of serum led to production of germ tubes by 40% of cap1/cap1 mutant yeasts at 5 h (arrow "5") and at 20 h the majority of yeasts had formed germ tubes that were shorter than those of the other strains (arrow "6"). Bars indicate a length of 5 $\mu$m.
Figure 6B:
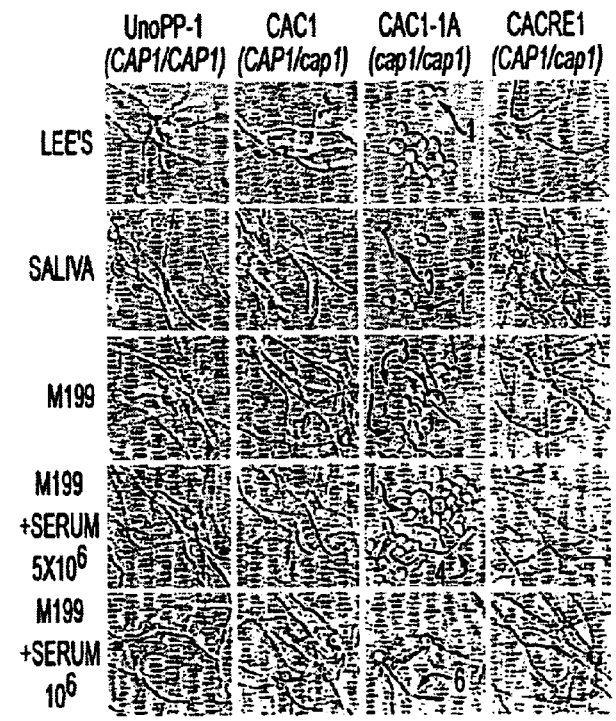

Mass conversion of yeasts to germ tubes (bud-hypha transitions) were performed in liquid media. cap1/cap1 mutants were unconditionally deficient in producing germ tubes in liquid suspension compared to CAP1/cap1 and CAP1/CAP1 strains. For the latter strains the percentages of yeasts with germ tubes approached 100% in Lee's media (pH 6.8), M199, M199 with 5% bovine serum albumin, and saliva (FIGS. 6A–6B). Media containing simple inducers also did not support germ tube production by cap1/cap1 yeasts. cap1/cap1 yeast cells in M199 with or without serum appeared elongated or pseudohyphal, but germ tubes were not seen. cap1/cap1 mutant cells budded in all conditions as determined by cell counting and differential labeling of parent yeasts with anti-C. albicans antiserum, permitting unlabeled nascent buds and yeasts produced during the incubation period to be distinguished from inoculum yeasts.

Upon prolonged incubation, germ tubes were found at low frequencies in cultures of the cap1/cap1 mutant (FIG. 6B). After 20 h of incubation in M199 and in saliva a few (<10%) CAP1 yeast cells had germ tubes. In M199 containing 5% serum the percentage was higher (approximately 20–30%), resembling cultures of wild type strains inoculated at cell concentrations that exceed the threshold for germ tube formation (Hazen et al., 24 Infect. Immun. 661–6 (1979)). Reducing the inoculum led to the emergence of germ tubes in approximately 40% of the cells after five hours of incubation in M199+serum. By nine hours most cap1/cap1 mutant cells (>80%) had formed germ tubes. Germ tubes of cap1/cap1 mutant cells were shorter in length than wild type germ tubes at 20 h. Further reductions in inoculum concentration did not lead to a higher frequency of germ tube formation. Germ tube formation in the cap1/cap1 mutant in the presence of serum was deficient in that the time to form germ tubes averaged four to five times longer and average frequencies of germ tube-forming cells were reduced for cap1/cap1 mutant cells compared to strains with CAP1. Similar results were found in 10% serum with 50 mM potassium phosphate buffer (pH 6.0).

The ability of cap1/cap1 mutant cells to form germ tubes upon prolonged incubation was limited to media containing serum. Lowering the cell concentration did not enhance germ tube formation in any other media tested, including saliva or M199 without serum.

The cap1/cap1 mutant was also unconditionally deficient in producing filamentous growth on agar-containing media (FIGS. 7A–7B). CAP1 strains grew predominantly as hyphae but in some cases, pseudohyphae were also seen. The term "filamentous growth" refers collectively to the production of pseudohyphae as well as true hyphae. The periphery of colonies with circular symmetry of CAP1 strains in Spider or M199 media consisted of extended hyphae with short branches whereas hyphae in SLAD had septae with numerous buds and thick-walled terminal buds resembling chlamydospores at hyphal tips. Characteristics of CAP1 strains in asymmetric colonies in serum media were mixed, consisting primarily of numerous branched hyphae bereft of buds and infrequent filaments coated with buds. The spectrum of morphological responses exhibited by strains with CAP1 was absent in colonies produced by cap1/cap1 mutant cells that consisted of budding yeasts independent of media composition. Strains with CAP1 formed filamentous growth on YPD agar as early as one week, but cap1/cap1 mutant colonies were devoid of filamentous growth even after two weeks of culture.

A single allele of CAP1 was sufficient for normal bud-hypha transitions and filamentous growth of C. albicans. Differences in the timing of germ tube emergence or in the length of hyphae in liquid media, or in colonial morphologies in agar media between strains with one or two copies of the CAP1 gene were not observed.

Measurement of Intracellular cAMP Levels During Germ Tube Induction.

Cytoplasmic cAMP levels were measured under conditions that induce germ tubes (M199 at 37° C.) or lead to budding (M199 at 27° C.) in wild type stains. Yeasts grown to middle logarithmic phase in M199 at 27° C. were used as the inoculum. Under germ tube inducing conditions, the majority of the cells (>95%) in strains with CAP1 had germ tubes by 3 h whereas cap1/cap1 cells produced buds (FIG. 8C).

Figure 8:
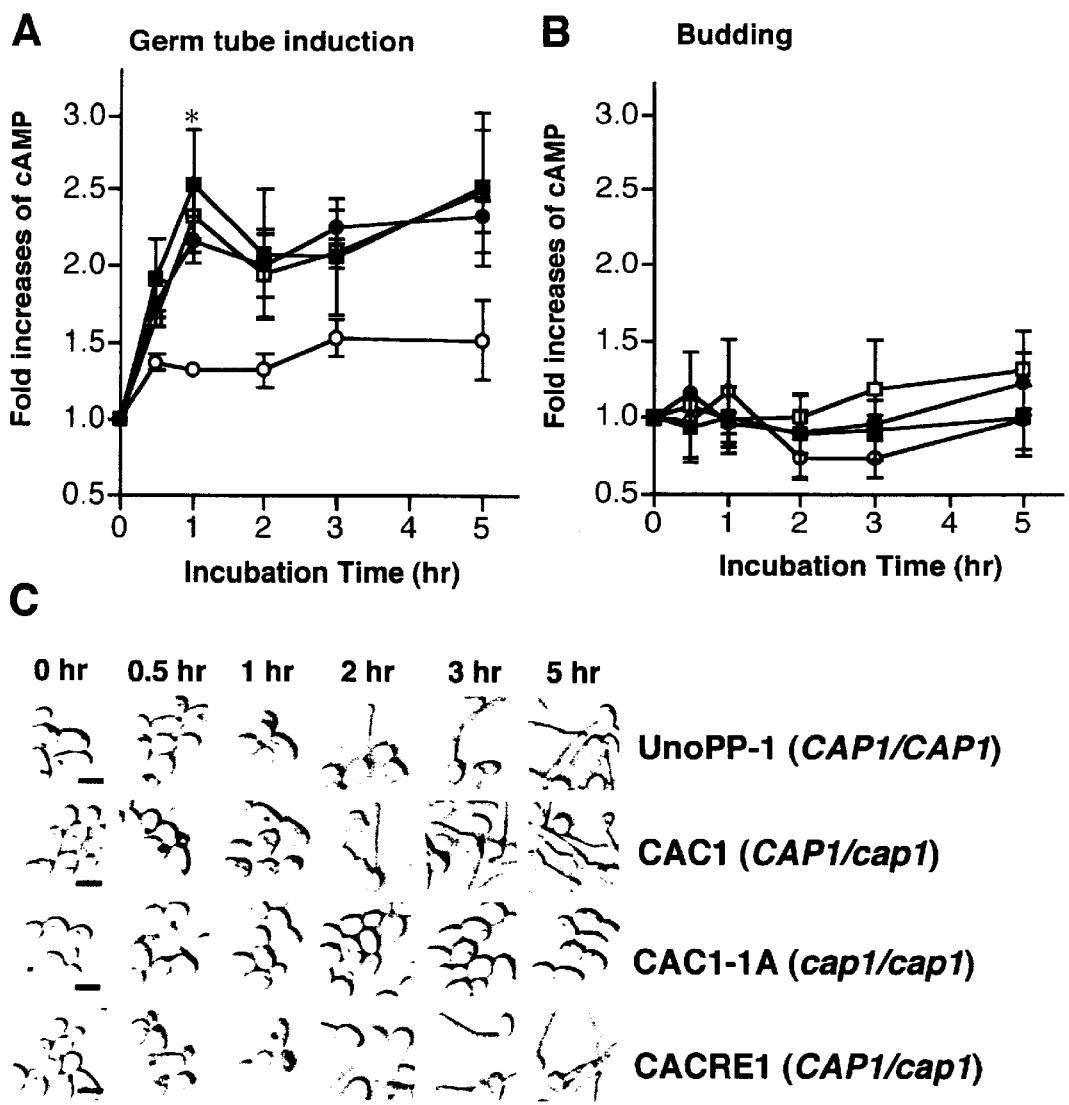
FIGS. 8A–8C depict the reduced cAMP levels of the *C. albicans* cap1/cap1 mutant in germ tube inducing conditions compared to strains with CAP1. Intracellular cAMP levels in each strain (UnoPP-1 (CAP1/CAP1, □), CAC1 (cap1/cap1, ■), CACRE1 (cap1/cap1, ●), and CAC1-1A (cap1/cap1, ○)) were measured. Each value in the Y axis indicates the fold increase in cAMP over the basal level in each strain at time zero. Error bars indicate the standard deviation of each value from three independent experiments performed in triplicate.

Intracellular cAMP levels of strains with CAP1 increased sharply after placement in induction conditions, peaking at levels that were 2 to 2.5 fold higher than initial concentrations at one hour (FIG. 8A). After a small decrease at two hours, cAMP levels gradually increased over the five-hour incubation period. Consistent with the results for germ tube induction described above, copy number effects were not seen for CAP1 in regulating cAMP levels prior to germ tube emergence. Significant differences in cAMP levels between CAP1/CAP1 and CAP1/cap1 strains were not observed. The cap1/cap1 mutant exhibited a small increase in cAMP at 30 min that plateaued, and achieved only a 1.5 fold increase over the five hour period.

The cAMP level increase in CAP1 strains was not seen under conditions where germ tubes were not induced (FIG. 8B).

Example 5

The effect of cAMP or dbcAMP on Colonial Morphologies and Bud-Hypha Transitions and of the cap1/cap1 Mutant.

If the reduced cAMP levels were responsible for the defective bud-hypha transitions and colonial morphologies, of the cap1/cap1 mutant, then exogenous addition of cAMP should reverse the defects. Both cAMP and dbcAMP dramatically altered the colony morphology of the cap1/cap1 mutant (FIG. 9A). Filamentous growth that closely resembled that of the positive control CAP1 strain was induced. The timing of onset of filamentous growth for CAP1 strains and for the cap1/cap1 mutant induced by cAMP and dbcAMP was the same, two days. dbcAMP was more dramatic in restoring filamentous growth to the cap1/cap1 mutant strain than cAMP (FIG. 9A), indicating that dbcAMP may be more efficiently taken up by cells than cAMP. Filamentous growth of the wild type strain also appeared to be slightly enhanced in the presence of cAMP and dbcAMP (FIG. 9A).

Hypha formation of the cap1/cap1 mutant in liquid media (M199+serum) was also enhanced by the addition of dbcAMP (10 mM). Hyphae of the cap1/cap1 mutant were much longer and more hyphae and pseudohyphae were seen if the media contained dbcAMP. The results appeared most dramatic at 13 h (FIG. 9B). At 3 h twice as many pseudohyphae were detected and the pseudohyphae were longer in the presence of dbcAMP. Thus the dbcAMP decreased the time required for emergence of filamentous structures. It was difficult to estimate the effect of exogenous dbcAMP on enhancing hyphal formation of the wild type strain because of extensive hyphae formation produced independent of the presence of dbcAMP (FIG. 9B). Exogenous cAMP (10 mM) produced similar but less dramatic effects on hyphal formation of the cap1/cap1 mutant.

These results are consistent with CAP1 regulation of bud-hypha transitions of *C. albicans* by modulating cAMP levels.

Example 6

CAP1 Gene is Required for Virulence in a Murine Model of Systemic Candidiasis.

The role of the CAP1 gene in the pathogenesis of systemic candidiasis was investigated using male CBA/J mice (5–6 weeks of age) as previously described (Staab et al., 283 Science 1535–8 (1999)). *C. albicans* strains (SC5314 (CAP1/CAP1), CAC1 (CAP1/cap1), CAC1-1A (cap1/cap1) and CACRE1 (CAP1/cap1, revertant)) were grown to stationary phase in peptone-dextrose (PD) media. Cells were then harvested, washed, and resuspended in 0.9% NaCl at a concentration of $10^6$ cells/ml. Four groups of mice (six per group) were injected via the lateral tail vein with $2 \times 10^5$ cells in a final volume of 200 μl in two independent studies. Survival was monitored daily. Kidney tissue were cultured on YPD plated to determine colony forming units (CFU) per gram of tissue and to verify germ tube formation phenotypes. Survival curves were illustrated by the Kaplan-Meier method using the PRISM program 2.0b (GraphPad Software, San Diego, Calif.) and statistical differences between paired groups were compared using the log-rank test.

Figure 10:
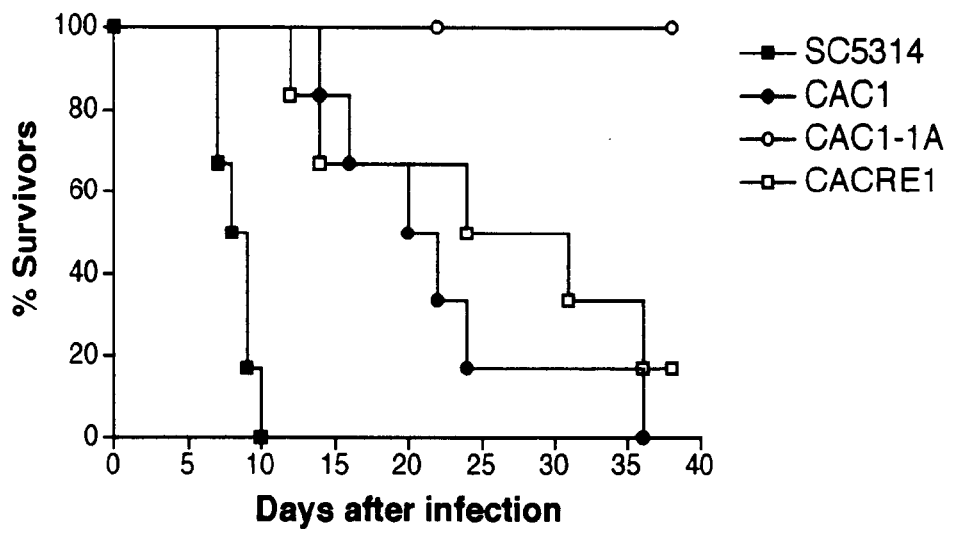
FIG. 10 depicts the survival curves of mice (CBA/J, 5–6 weeks of age) infected with $2 \times 10^5$ cells of *C. albicans* strains SC5314 (CAP1/CAP1; n=6), CAC1 (CAP1/CAP1; n=6), CAC1-1A (cap1/cap1; n=6), and CACRE1 (CAP1/CAP1, revertant; n=6). Similar results were obtained in two independent experiments. Survival curves were illustrated according to the Kaplan-Meier method using the PRISM program and compared using the log-rank test. A p value <0.05 was considered significant.

Mice injected with the wild type *C. albicans* strain (SC5314) expired within 10 days after injection (FIG. 10). C albicans strains with a single copy of the CAP1 gene (CAC1 and CACRE1) showed reduced virulence when compared with the parental CAP1/CAP1 strain (p=0.0006) but 80% of the mice became ill and were sacrificed by 35 days (FIG. 10). In contrast, six mice given the cap1/cap1 mutant survived and behaved normally during the entire period of observation (FIG. 10). Survival of mice injected with the cap1/cap1 mutant was significantly reduced relative to control strains (SC5314 vs. CAC1-1A, p=0.0006; CAC1 vs. CAC1-1A, p=0.0007; CACRE1 vs. CAC1-1A, p=0.0069). No statistically significant difference was found between the heterozygous CAP1/CAP1 mutant (CAC1) and the revertant (CACRE1) (p=0.3661). Colony-forming units of *C. albicans* were detected in sacrificed mice injected with CAP1 strains ($10^7$ cfu per gram kidney). Of the 6 mice injected with the cap1/cap1 mutant, three had infected kidneys ($1.9 \times 10^8$ cfu per gram kidney) and three cleared the infection. Yeasts isolated from kidneys of mice that received the cap1/cap1 mutant showed the same defects in forming germ tubes as those used for intravenous injection, verifying the authenticity of strains and the importance of delayed germ tube formation in virulence.

The avirulence of the cap1/cap1 mutant extends the findings of other studies (Calera et al., 68 Infect. Immun. 518–25 (2000); Calera et al., 67 Infect. Immun. 4280–4 (1999); Lo et al., 90 Cell 939–49 (1997); Schweizer et al., 38 Mol. Microbiol. 435–45 (2000); Yamada-Okabe et al., 181 J. Bacteriol. 7243–7 (1999)) in showing that the ability to produce hyphae with normal kinetics as well as the absolute ability to produce hyphae is important for candidiasis. The avirulence of cap1/cap1 mutants is also supportive of an important role for the cAMP signaling pathway in growth of *C. albicans* in host tissue. The rapid production of hypha-specific factors such as the Hwp1 adhesin (Staab et al., Science, supra) and others (Schaller et al., 34 Mol. Microbiol. 169–80 (1999); Staib et al., supra) coincident with germ tube formation are likely to be important for systemic candidiasis in mice. The virulence study shows that *C. albicans* joins other pathogenic fungi in the involvement of the cAMP signaling pathway in pathogenesis. Disruption of the gene encoding the catalytic subunit of cAMP dependent PKA and disruption of the GPA1 gene affect the virulence of *M. grisea*, and *Cryptococcus neoformans*, respectively.

Example 7

Gene Expression Analysis

Gene expression analysis using microarray technology may be useful in the context of a diagnostic kit for candidiasis or to affirm expression or lack thereof of mutant strains of *C. albicans*. It is desirable to include in the sample of target nuclei acids, a labeled set of standard DNA molecules that are present in known amounts and can be used as calibrating agents in subsequent analysis. The standard may be provided by reverse transcribing the standard RNA into end-labeled cDNA under conditions substantially the same as, and preferably identical to, the conditions used to prepare the labeled target nucleic acid sample. The resultant end-labeled standard is then printed in an allocated area of the microarray.

Methods of isolating RNA from cells, tissues, organs or whole organisms are known to those of skilled in the art and are described in Sambrook et al., (supra). Isolated sample mRNA is reverse transcribed into end-labeled target nucleic acid by hybridizing an appropriately labeled oligo(dT) primer to the mRNA under conditions sufficient for enzymatic extension of the hybridized polymer. The primer is sufficiently long to provide for efficient hybridization to the polyA tail. Alternatively, for amplification of fragments of sample mRNA, one may optionally provide for a short sequence 3' of the oligo dT region, where the dNTP immediately adjacent to the oligo dT region will not be a dTTP and usually the sequence will comprise no dTTP. The primer will carry the label, as described above. The primer is incubated with the mRNA in the presence of reverse transcriptase and other reagents necessary for primer extension under conditions sufficient for first strand cDNA synthesis, where additional reagents include dNTPs; buffering agents, e.g. Tris.Cl; cationic sources, both monovalent and divalent, e.g. KCl, $MgCl_2$; RNAase inhibitor and sulfhydril reagents, e.g. dithiothreitol; and the like. DNA polymerase can be used for the first strand cDNA synthesis step.

First stand synthesis is completed by adding isolated RNA and the appropriate primer. The primer/RNA mix is incubated followed by the addition of first strand reaction buffer, DTT, dNTPs, RNasin, and Superscript II (Gibco BRL) to the mix. Following a second incubation period, second strand synthesis buffer, dNTPs, DNA polymerase, RNase, DNA ligase, and RNase-free water are added. Following a third incubation period, DNA polymerase is added to each sample. Following a fourth incubation period, the cDNA is extracted and washed 3×with water in a column. After collection from the column, the cDNA is dried for in vitro transcription.

A transcription kit may be used to amplify RNA. In a microfuge tube, double-stranded cDNA, RNA polymerase buffer, ATP, CTP, GTP, UTP, DTT, and RNA polymerase are added and then incubated. The amplified RNA is washed 3×in a column, collected, and dried.

Amplified RNA (aRNA) from the first round amplification is mixed with random hexamers, incubated, chilled on ice, and then equilibrated at room temperature. For the initial reaction, first stand buffer, DTT, dNTPs, RNasin, and reverse transcriptase are added to the aRNA mix, and then incubated. RNase is then added and the sample is incubated again. For second strand cDNA synthesis, primer is added to the aRNA reaction mix and the sample is incubated. Second strand synthesis buffer, dNTPs, DNA Polymerase, RNase, DNA ligase, and RNase-free water are added to the sample mix and the sample is incubated again. DNA polymerase is then added followed by sample incubation. The double-stranded cDNA is extracted to remove extraneous protein and purified to remove the unincorporated nucleotides and salts.

aRNA and random hexamers are mixed in a solution containing RNase-free water, heated, and then chilled on ice. For the labeling reaction, first strand buffer, DTT, RNasin, d(GAT)TP, dCTP, labeled-dCTP, and reverse transcriptase are added to the aRNA mix and incubated at room temperature. The aRNA template is degraded and the sample incubated again at a suitable temperature. The probes are purified with Microcon 30 Columns and Qiagen Nucleotide Removal Columns. The probes are vacuum-dried and resuspend in hybridization buffer.

Microarray matrices are treated to ensure amino-linkage of cDNAs to the slides, and then are boiled in water to denature the cDNA. Labeled probes are heated, cooled to room temperature, and then applied to the slides. The slides are covered with glass cover slips, sealed with DPX (Fluka) and hybridized.

At the end of hybridization, the slides are cooled to room temperature. The slides are washed and are ready for scanning. In order to evaluate the relationship between hybridization signal and sample probe concentration, hybridization intensity is measured as a function of concentration of the RNAs for one or more of the target genes. Sample RNA concentration is compared with standard RNA concentration to determine expression level.

Example 8

Identify Potential Virulence Genes that are Activated by Signaling Pathways Involving Cap1 Protein Using Microarray Technology.

By way of example, one may identify potential virulence genes that are activated by signaling pathways involving Cap1 protein using microarray technology. The strategy is to compare mRNA's from the cap1 gene null mutants to parent strain mRNA to identify individual transcripts that are absent in the mutant and present in the parent or in the heterozygous CAP1/cap1 gene mutant. The basic approach is to use RNA from the isogenic strains with or without the Cap1s that were grown in hyphae-inducing conditions, such as M199 at 37 degrees C., to prepare labeled cDNA. RNA samples are taken at 1 and 2 h after induction. The analysis for this approach involves the identification of transcripts that are absent or greatly reduced in the mutant compared to the other strains using microarrays. The microarrays may be used to compare gene expression in the mutant to parental and/or revertant strains.

Figure 11:
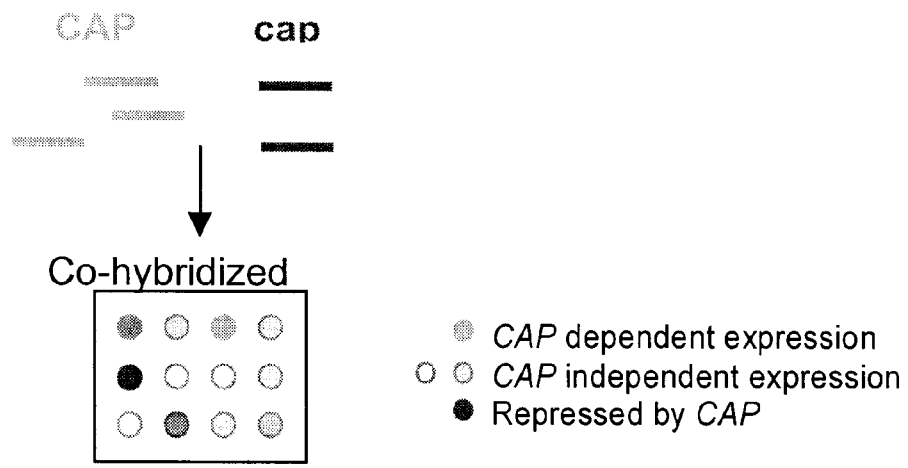
FIG. 11 depicts the identification of potential virulence genes that are activated by signaling pathways involving Cap1 protein using microarray technology.

*C. albicans* microarrays are produced by methods known to those skilled in the art. For comparing gene expression in the CAP1 gene null mutants to parental or revertant strains, poly $A^+$ mRNA from the two strains are reverse transcribed to form cDNA's which are labeled with different fluorescent dyes (red Cy3 for the mutant reference cDNA or green Cy5 for the strain with a wild type CAP1 gene) and co-hybridized onto a single array as previously described to be read with a confocal laser scanning microscope (see FIG. 11). The quantitative ratio of green to red signal for each spot (gene) reflects the relative abundance of the each labeled cDNA hybridized to the spot (gene) between the two experimental samples. A gene whose transcription depends on Cap1 is greatly reduced in the cap1/cap1 mutant compared to the parent or revertant, and will hybridize a relative abundance of green wavelength-labeled cDNA compared to genes whose expression do not depend on the mutated gene. Virulence genes (or housekeeping genes that are controlled by the CAP1 gene) will also give high green to red ratios, genes that do not depend on the CAP1 gene will be equally abundant in green and red wavelengths, appearing yellow, and genes that are repressed by the CAP1 gene will have a low abundance of green color and will be red.

HWP1 DNA serves as a standard for the degree of difference (ratio of green dye-labeled cDNA in the parental relative to the mutant strain) that would be expected for other genes regulated in a similar manner and to verify that the design successfully identifies genes controlled by the CAP1 gene.

To confirm the results from array experiments, the identified putative virulence genes are cloned and used to prepare probes for Northern blotting, to show that their transcripts have the predicted pattern of expression in the CAP1 mutant compared to the parental strain. The genes that depend on Cap1 for expression are analyzed by standard homology searches in order to gain insight into the functional category of the gene product; cell wall protein, metabolism, signal transduction, secretion and others. Genes that are predicted to function specifically in host interactions and have motifs suggestive of adhesins, proteinases, phospholipases, and those that resist toxic oxygen and nitrogen radicals produced during host defense are selected for creation of null mutants and virulence assays in animal models. In contrast, housekeeping genes will not be pursued for a role in pathogenesis, but will be used to predict metabolic pathways employed by *C. albicans* when growing in host cells. The identity of the genes will form the bases of new hypotheses about pathogenic mechanisms that will be directly testable in the following aim. These experiments have a very high probability of revealing a Cap1-dependent set of genes that *C. albicans* deploys that permits invasion and proliferation in host tissues.

Mini and microarray approaches to pathogenic questions will be extremely important for advancing knowledge about

*C. albicans* because of the present inability to employ random mutagenesis approaches with this diploid organism. Furthermore, the availability of membranes and/or chips for *C. albicans* is imminent.

Various modifications and variations of the described methods and systems of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

The disclosures of all references and publications cited above are expressly incorporated by reference in their entireties to the same extent as if each were incorporated by reference individually.

SEQUENCE LISTING

<160> NUMBER OF SEQ ID NOS: 2

<210> SEQ ID NO 1
<211> LENGTH: 545
<212> TYPE: PRT
<213> ORGANISM: Candida albicans

<400> SEQUENCE: 1

```
Met Ser Thr Glu Glu Ser Gln Phe Asn Val Gln Gly Tyr Asn Ile Ile
1               5                   10                  15

Thr Ile Leu Lys Arg Leu Glu Ala Ala Thr Ser Arg Leu Glu Asp Ile
            20                  25                  30

Thr Ile Phe Gln Glu Glu Ala Asn Lys Asn His Tyr Gly Val Asp Ser
        35                  40                  45

Leu Thr Glu Lys Gly Thr Pro Lys Ser Arg Thr Val Glu Ser Ser Glu
    50                  55                  60

Ala Thr Ser Asp Gly Lys Ser Leu Glu Ser Thr Ser Phe Ala Thr Phe
65                  70                  75                  80

Ser Glu Ala Pro Val Glu Lys Ser Lys Leu Ile Val Glu Phe Glu Asn
                85                  90                  95

Phe Val Glu Ser Tyr Val His Pro Leu Val Glu Thr Ser Lys Lys Ile
            100                 105                 110

Asp Ser Leu Val Gly Glu Ser Ala Gln Tyr Phe Tyr Glu Ala Phe Val
        115                 120                 125

Glu Gln Gly Lys Phe Leu Glu Leu Val Leu Gln Ser Gln Gln Pro Asp
    130                 135                 140

Met Thr Asp Pro Ala Leu Ala Lys Ala Leu Glu Pro Met Asn Ala Lys
145                 150                 155                 160

Cys Thr Lys Ile Asn Glu Leu Lys Asp Ser Asn Arg Lys Ser Pro Phe
                165                 170                 175

Phe Asn His Leu Ser Thr Phe Ser Glu Ser Asn Ala Val Phe Tyr Trp
            180                 185                 190

Ile Gly Ile Pro Thr Pro Val Ser Tyr Ile Thr Asp Thr Lys Asp Thr
        195                 200                 205

Val Lys Phe Trp Ser Asp Arg Val Leu Lys Glu Tyr Lys Thr Lys Asp
    210                 215                 220

Gln Val His Val Glu Trp Val Lys Gln Thr Leu Ser Val Phe Asp Glu
225                 230                 235                 240

Leu Lys Asn Tyr Val Lys Glu Tyr His Thr Thr Gly Val Ala Trp Asn
                245                 250                 255

Pro Lys Gly Lys Pro Phe Ala Glu Val Val Ser Gln Gln Thr Glu Ser
            260                 265                 270

Ala Ala Lys Asn Ser Ser Ser Ala Ser Gly Ser Ala Gly Gly Ala Ala
        275                 280                 285
```

```
Pro Pro Pro Pro Pro Pro Pro Pro Ala Thr Phe Phe Asp Asp Thr
    290                 295                 300
Glu Lys Asp Ser Glu Asn Pro Ser Pro Ala Ser Gly Gly Ile Asn Ala
305                 310                 315                 320
Val Phe Ala Glu Leu Asn Gln Gly Ala Asn Ile Thr Ser Gly Leu Lys
                325                 330                 335
Lys Val Asp Lys Ser Glu Met Thr His Lys Asn Pro Glu Leu Arg Lys
            340                 345                 350
Gln Pro Pro Val Ala Pro Lys Lys Pro Ala Pro Lys Lys Pro Ser
        355                 360                 365
Ser Leu Ser Gly Gly Val Ser Ser Ala Pro Val Lys Lys Pro Ala Lys
    370                 375                 380
Lys Glu Leu Ile Asp Gly Thr Lys Trp Ile Ile Gln Asn Phe Thr Lys
385                 390                 395                 400
Ala Asp Ile Ser Asp Leu Ser Pro Ile Thr Ile Glu Val Glu Met His
                405                 410                 415
Gln Ser Val Phe Ile Gly Asn Cys Ser Asp Val Thr Ile Gln Leu Lys
            420                 425                 430
Gly Lys Ala Asn Ala Val Ser Val Ser Glu Thr Lys Asn Val Ala Leu
        435                 440                 445
Val Ile Asp Ser Leu Ile Ser Gly Val Asp Val Ile Lys Ser Tyr Lys
    450                 455                 460
Phe Gly Ile Gln Val Leu Gly Leu Val Pro Met Leu Ser Ile Asp Lys
465                 470                 475                 480
Ser Asp Glu Gly Thr Ile Tyr Leu Ser Gln Glu Ser Ile Asp Asn Asp
                485                 490                 495
Ser Gln Val Phe Thr Ser Ser Thr Ala Leu Asn Ile Asn Ala Pro
            500                 505                 510
Lys Glu Asn Asp Asp Tyr Glu Glu Leu Ala Val Pro Glu Gln Phe Val
        515                 520                 525
Ser Lys Val Val Asn Gly Lys Leu Val Thr Gln Ile Val Glu His Ala
    530                 535                 540
Gly
545

<210> SEQ ID NO 2
<211> LENGTH: 1638
<212> TYPE: DNA
<213> ORGANISM: Candida albicans

<400> SEQUENCE: 2
atgtcaaccg aggagagtca attcaatgtt caaggttaca atattatcac aatcttgaaa     60
agattagagg cagcaacgtc tcgtcttgag gacattacca ttttccaaga ggaagcaaac    120
aaaaaccact atggagttga ttctctcact gaaaagggaa cccccaaaag cagaactgtt    180
gaatcgtcag aagcaacttc cgatggtaaa tcactcgaat ctacatcatt tgccactttt    240
tctgaagctc ctgtagaaaa atccaaattg attgtggaat tgagaacttt gttgaaagc    300 tacgttcatc cacttgttga acatccaaaa agatcgatt ccttggtggg ggagtccgcc    360
caatattttt atgaggcatt tgtcgaacaa gggaaatttt tggagcttgt attgcaatcc    420
caacaaccag atatgactga tccagctttg gcaaaggcat tagaaccaat gaatgctaaa    480
tgcaccaaaa ttaacgaatt aaaagattcc aatcgtaaat ctccattctt caatcattta    540
agcactttca gtgaaagtaa tgccgttttt tattggattg ggatccctac accagtctcg    600
```

```
tacattactg atactaaaga tacagtcaaa ttttggtctg acagagtttt aaaagaatac    660
aagaccaaag accaagtgca tgttgaatgg gtaaaacaaa cattatctgt ttttgacgaa    720
ttgaagaatt atgttaaaga atatcacaca actggtgttg cttggaaccc caaaggaaag    780
ccttttgcag aagttgtatc tcagcaaaca gagagtgctg ctaagaattc ttcgtctgct    840
tctggttctg caggaggagc agctccacca ccacctccac ctccacctcc agcaacgttt    900
tttgatgaca ctgaaaaaga cagtgaaaat ccatctccag cttcaggtgg tattaatgcg    960 gttttgctg aattgaatca aggtgccaac atcacatctg gtttaaaaaa agtcgacaaa   1020
tctgagatga cgcataagaa ccctgaatta agaaaacagc caccagttgc accaaaaaaa   1080
ccagcacccc caaagaagcc atctagttta tccggtggtg tgagttcagc tccagtaaag   1140
aagcctgcta agaaggagtt gattgacggt acaaaatgga taattcaaaa ttttacaaaa   1200
gctgatattt ccgatttgag tccaattacc attgaagttg agatgcatca atctgttttc   1260
attggtaatt gtagtgatgt caccattcag ttgaaaggta aagcaaatgc agtgtcggta   1320
tcggaaacca agaatgtggc tcttgtcatt gattcgttga tttccggagt cgatgttatt   1380
aaatcctaca agtttggtat acaagtttta ggtttggtac caatgttgag tattgataaa   1440
tcagatgaag ggactatcta tttgtcgcaa gaaagcattg acaatgatag tcaggttttt   1500
actagtagca ctacagcact caacatcaat gcaccaaagg aaaatgatga ttatgaagaa   1560
ttggctgttc ctgaacaatt tgttagtaag gttgtgaatg gcaaattagt cactcaaatt   1620
gttgaacatg ctggataa                                                1638
```

I claim:

1. A method for interfering with morphogenic transitions of *Candida albicans* comprising the step of:
disrupting a gene associated with the cyclic AMP pathway upon which said *Candida albicans* relies for morphogenic transition.

2. The method of claim 1, wherein said method further comprises the step of reducing the virulent properties of said *Candida albicans*.

3. The method of claim 2, wherein said virulent properties comprise adhesive properties.

4. The method of claim 3, wherein said adhesive properties comprise abilities of *Candida albicans* to adhere to one or more human tissues.

5. The method of claim 4, wherein said human tissues are one or more human tissues selected from the group consisting of vaginal, penile, oral, esophageal, gastrointestinal, and umbilical tissues.

6. The method of claim 2, wherein said virulent properties comprise invasive properties.

7. The method of claim 6, wherein said invasive properties comprise abilities of *Candida albicans* to degrade extracellular matrix proteins.

8. The method of claim 6, wherein said invasive properties comprise abilities of *Candida albicans* to block neutrophil oxygen radical production and degranulation.

9. The method of claim 2, wherein said virulent properties comprise proliferative properties.

10. The method of claim 9, wherein said proliferative properties comprise abilities of *Candida albicans* cells to induce their exit from other cells that have engulfed said *Candida albicans* cells.

11. The method of claim 10, wherein said exit from other cells comprises the physical interaction by *Candida albicans* cells of said other cells by hyphae.

12. The method of claim 1, wherein said *Candida albicans* is a pathogenic yeast strain.

13. The method of claim 1, wherein said morphogenic transitions comprise transitions from the budding form to the hyphal growth form.

14. The method of claim 1, wherein said biochemical signaling pathways comprise cAMP-PKA signaling pathways said *Candida albicans*.

15. The method of claim 14, wherein said interfering with said multifunctional cAMP-PKA signaling or other Cap1 function pathways of *Candida albicans* comprises the disruption of a gene associated with said pathway.

16. The method of claim 15, wherein said gene comprises the *C. albicans* homolog of adenylate cyclase-associated protein (CAP1) gene.

17. The method of claim 16, wherein said disruption comprises interfering with the coding region of said *C. albicans* homolog of adenylate cyclase-associated protein (CAP1) gene.

18. The method of claim 16, wherein said homolog comprises the following isolated DNA sequence SEQ. ID NO. 2:

```
ATGTCAACCGAGGAGAGTCAATTCAATGTTCAAGGTTACAATATTATCAC

AATCTTGAAAAGATTAGAGGCAGCAACGTCTCGTCTTGAGGACATTACCA

TTTTCCAAGAGGAAGCAAACAAAAACCACTATGGAGTTGATTCTCTCACT

GAAAAGGGAACCCCCAAAAGCAGAACTGTTGAATCGTCAGAAGCAACTTC

CGATGGTAAATCACTCGAATCTACATCATTTGCCACTTTTTCTGAAGCTC
```

-continued
```
CTGTAGAAAAATCCAAATTGATTGTGGAATTTGAGAACTTTGTTGAAAGC

TACGTTCATCCACTTGTTGAAACATCCAAAAAGATCGATTCCTTGGTGGG

GGAGTCCGCCCAATATTTTTATGAGGCATTTGTCGAACAAGGGAAATTTT

TGGAGCTTGTATTGCAATCCCAACAACCAGATATGACTGATCCAGCTTTG

GCAAAGGCATTAGAACCAATGAATGCTAAATGCACCAAAATTAACGAATT

AAAAGATTCCAATCGTAAATCTCCATTCTTCAATCATTTAAGCACTTTCA

GTGAAAGTAATGCCGTTTTTTATTGGATTGGGATCCCTACACCAGTCTCG

TACATTACTGATACTAAAGATACAGTCAAATTTTGGTCTGACAGAGTTTT

AAAAGAATACAAGACCAAAGACCAAGTGCATGTTGAATGGGTAAAACAAA

CATTATCTGTTTTTGACGAATTGAAGAATTATGTTAAAGAATATCACACA

ACTGGTGTTGCTTGGAACCCCAAAGGAAAGCCTTTTGCAGAAGTTGTATC

TCAGCAAACAGAGAGTGCTGCTAAGAATTCTTCGTCTGCTTCTGGTTCTG

CAGGAGGAGCAGCTCCACCACCACCTCCACCTCCACCTCCAGCAACGTTT

TTTGATGACACTGAAAAAGACAGTGAAAATCCATCTCCAGCTTCAGGTGG

TATTAATGCGGTTTTGCTGAATTGAATCAAGGTGCCAACATCACATCTGG

TTTAAAAAAAGTCGACAAATCTGAGATGACGCATAAGAACCCTGAATTAA

GAAAACAGCCACCAGTTGCACCAAAAAAAACCAGCACCCCCAAAGAAGCC

ATCTAGTTTATCCGGTGGTGTGAGTTCAGCTCCAGTAAAGAAGCCTGCTA

AGAAGGAGTTGATTGACGGTACAAAATGGATAATTCAAAATTTTACAAAA

GCTGATATTTCCGATTTGAGTCCAATTACCATTGAAGTTGAGATGCATCA

ATCTGTTTTCATTGGTAATTGTAGTGATGTCACCATTCAGTTGAAAGGTA

AAGCAAATGCAGTGTCGGTATCGGAAACCAAGAATGTGGCTCTTGTCATT

GATTCGTTGATTTCCGGAGTCGATGTTATTAAATCCTACAAGTTTGGTAT

ACAAGTTTTAGGTTTGGTACCAATGTTGAGTATTGATAAATCAGATGAAG

GGACTATCTATTTGTCGCAAGAAAGCATTGACAATGATAGTCAGGTTTTT

ACTAGTAGCACTACAGCACTCAACATCAATGCACCAAAGGAAATGATGAT

TATGAAGAATTGGCTGTTCCTGAACAATTTGTTAGTAAGGTTGTGAATGG

CAAATTAGTCACTCAAATTGTTGAACATGCTGGATAA.
```

19. The method of claim 16, wherein said homolog encodes a polypeptide having the following sequence (SEQ. ID. NO. 1):

```
MSTEESQFNVQGYNIITILKRLEAATSRLEDITIFQEEANKNHYGVDSLT

EKGTPKSRTVESSEATSDGKSLESTSFATFSEAPVEKSKLIVEFENFVES

YVHPLVETSKKIDSLVGESAQYFYEAFVEQGKFLELVLQSQQPDMTDPAL

AKALEPMNAKCTKINELKDSNRKSPFFNHLSTFSESNAVFYWIGIPTPVS
```

-continued
```
YITDTKDTVKFWSDRVLREYKTKDQVHVEWVKQTLSVFDELKNYVKEYHT

TGVAWNPKGKPFAEVVSQQTESAAKINSSSASGSAGGAAPPPPPPPPPAT

FFDDTEKDSENPSPASGGINAVFAELNQGANITSGLKKVDKSEMTHKNPE

LRKQPPVAPKKPAPPKKPSSLSGGVSSAPVKKPAKKELIDGTKWIIQNFT

KADISDLSPITIEVEMHQSVFIGNCSDVTIQLKGKANAVSVSETKNVALV

IDSLISGVDVIKSYKFGIQVLGLVPMLSIDKSDEGTIYLSQESIDNDSQV

FTSSTTALNINAPKENDDYEELAVPEQFVSKVVNGKLVTQIVEHAG.
```

20. The method of claim 14, wherein said cAMP-PKA signaling pathways operate to increase levels of cAMP.

21. The method of claim 20, wherein said increased levels of cAMP operate to stimulate morphogenic transitions of *Candida albicans*.

22. The method of claim 1, wherein said biochemical signaling pathway is within *Candida albicans* that has infected a human.

23. The method of claim 22, wherein said human suffers from a disease.

24. The method of claim 23, wherein said disease is human immunodeficiency virus.

25. The method of claim 23, wherein said disease comprises complications associated with acquired immune deficiency syndrome.

26. The method of claim 23, wherein said disease comprises complications associated with an acquired immune deficiency syndrome related complex.

27. The method of claim 23, wherein said disease comprises one or more diseases selected from the group consisting of acquired immune deficiency syndrome, mucosal candidiasis, oral candidiasis, esophageal candidiasis, thrush, hemoatogenously disseminated candidiasis, and candida vaginitis.

28. The method of claim 22, wherein said human is immunocompromised.

29. The method of claim 22, wherein said human is an organ transplant recipient.

30. The method of claim 22, wherein said human is undergoing a treatment regimen.

31. The method of claim 30, wherein said treatment regimen is chemotherapy.

32. The method of claim 30, wherein said treatment regimen is a drug regimen.

33. The method of claim 32, wherein said drug regimen suppresses the immune system.

34. The method of claim 32, wherein said treatment regimen incorporates the use of one or more treatments that are selected from the group consisting of azathioprine, steroids, cyclosporine, antilymphocyte globulins, monoclonal anti-T cell antibodies, prednisone, methylprednisone, and cyclophosphamide.

* * * * *

UNITED STATES PATENT AND TRADEMARK OFFICE
CERTIFICATE OF CORRECTION

PATENT NO. : 6,706,688 B2  Page 1 of 1
APPLICATION NO. : 09/801774
DATED : March 16, 2004
INVENTOR(S) : Sundstrom et al.

It is certified that error appears in the above-identified patent and that said Letters Patent is hereby corrected as shown below:

At column 1, line 12, please delete "2R01DE011375" and insert --R01A1046608--.

Signed and Sealed this

Twentieth Day of May, 2008

JON W. DUDAS
*Director of the United States Patent and Trademark Office*